United States Patent [19]
Elsbach et al.

[11] Patent Number: 5,489,676
[45] Date of Patent: Feb. 6, 1996

[54] POLYPEPTIDES THAT POTENTIATE BACTERICIDAL/PERMEABILITY-INCREASING PROTEIN AND METHODS FOR TREATING BACTERIAL INFECTIONS

[76] Inventors: Peter Elsbach, 440 E. 23rd St., New York, N.Y. 10010; Chean Eng Ooi, 268 Marlborough Rd., Brooklyn, N.Y. 11226; Jerrold Weiss, 8 Stuyvesant Oval, New York, N.Y. 10009

[21] Appl. No.: 23,760

[22] Filed: Feb. 26, 1993

Related U.S. Application Data

[63] Continuation-in-part of Ser. No. 905,066, Jun. 24, 1992, abandoned, which is a continuation-in-part of Ser. No. 767,551, Sep. 26, 1991, abandoned, which is a continuation of Ser. No. 502,560, Mar. 30, 1990, abandoned.

[51] Int. Cl.$^6$ .......................... C12P 21/06; C07H 19/00; C07H 21/00; A61K 38/00
[52] U.S. Cl. .................. 536/22.1; 435/7.3; 435/69.6; 530/324; 536/23.1; 536/23.2; 536/23.5
[58] Field of Search ................... 435/7.3, 69.6; 514/12, 21; 530/324; 536/22.1, 23.1, 23.2, 23.5

[56] References Cited

U.S. PATENT DOCUMENTS 5,089,274  2/1992  Marra et al. ..................... 424/534

FOREIGN PATENT DOCUMENTS 0272489  6/1988  European Pat. Off.

OTHER PUBLICATIONS

Tobias et al., *J. Biol. Chem.*, 263:13479–13481, 1988.
Marra et al., *J. Immunol.*, 144:662–666, 1990.
Weiss et al., *Blood*, 69:652–659, 1987.
Mannion et al., *J. Immunol.*, 142:2807–2812, 1989.
Gray et al., *J. Biol. Chem.*, 264:9505–9509, 1989.
Tobias et al., *J. Biol. Chem.*, 264:10867–10871, 1989.
Veld et al., *Infection and Immunity*, 56:1203–1208, 1988.
Elsbach, *Trends in Biotechnology*, 8:26–30, 1990.
Weiss et al., *Infection and Immunity*, 51:594–599, 1986.
Farley et al., *Infection and Immunity*, 56:1589–1592, 1988.
Weiss et al., *J. Clin. Invest.*, 65:619–628, 1980.
Weiss et al., *Infection and Immunity*, 38:1149–1153, 1982.
Weiss et al., *J. of Immunol.*, 132:3109–3115, 1984.
Weiss et al., *J. Clin. Invest.*, 71:540–549, 1983.
Elsbach, *Bacteria–Host Cell Interaction*, 64:47–60, 1987.
Elsbach, et al., *Inflammation: Basic Prin. and Clin. Correlates*, 445–470, 1988.
Gabay et al., *Euro. J. of Clin. Invest.*, 18:A38, 1988.
Gray et al., *Clin. Res.*, 36:620A, 1988.
Ooi et al., *J. Biol. Chem.*, 262(31):14891–14894, 1987.
Shafer et al., *Infection and Immunity*, 43:834–838, 1984.
Spitznagel et al., *J. of Immunol.*, 139(4):1291–1296, 1988.
Ulevitch et al., *Progress Clin. Biol. Res.*, 272:309–318, 1988.
Weiss et al., *J. Clin. Invest.*, 55:33–42, 1975.
Weiss et al., *J. Biol. Chem.*, 253(8):2664–2672, 1978.
Weiss and Goldberg—Klein et al., *Clin. Res.*, 34:537A, 1986.
Weiss et al., *Clin. Res.*, 34:537A, 1986.
Olsson et al. CA:77(a):57921v (1972).
Walton et al., CA:90:20611m (1979).

*Primary Examiner*—Robert A. Wax
*Assistant Examiner*—Hyosuk Kim
*Attorney, Agent, or Firm*—Darby & Darby

[57] ABSTRACT

Disclosed herein are purified isolated mammals polypeptides having the property of potentiating the bacterial growth inhibitory activity of bactericidal/permeability-increasing protein and pharmaceutical formulations comprising these polypeptides. Also disclosed is a method for obtaining mammalian polypeptides having the property of potentiating the bacterial growth inhibitory activity of bactericidal/permeability-increasing protein potentiating activity, and methods for treating gram-negative bacterial infections in mammals and for neutralizing lipopolysaccharides. Also disclosed is a method for the treatment of diseases caused by endotoxins in mammals.

2 Claims, 19 Drawing Sheets

FIG. 14

```
1                                                                    CAGAAGCA          8
                                                                          A
9'     ATGGCAGGGGTCTCTGGAAGGTACTAGTGTGTGCTGGTGGGCTTGGCAGTGGTGGCTTGTGCCATCCCCGTCGCCGT    83'
9      M  A  G  V  W  K  V  L  V  V  L  V  G  L  A  V  V  A  C  A  T  P  R  R  R      83
                                                                         H

84'    CTGAGATATGAGGAGGTTGTGGCCCAGGCCCTTGCAGTTCTACAATGAGGGCAACAGGGCCAGCCCCTCTTCCGC      158'
84     L  R  Y  E  E  V  V  A  Q  A  L  Q  F  Y  N  E  G  Q  Q  Q  P  L  F  R          158

159'   CTGCTGGAAGCCACCCCACCCCCACCTAGTCTGAACTCTGAACTCCAGGATCCCAACTTCAGGATTAAAGAGACG      233'
159    L  L  E  A  T  P  P  C  S  L  N  S  K  S  R  I  P  L  N  F  R  I  K  E  T      233

234'   GTGTGCATTTTCACTCTGGACAGAGACCAGCCTGGAAACTGTGCCTTCAGAGAGGGGGAGGAGCGAATCTGCAGG      308'
234    V  C  I  F  T  L  D  R  Q  P  G  N  C  A  F  R  E  G  G  E  E  R  I  C  A      308
                                A
309'   GGCGCGTTCGTCAGGCGCAGGTGGGTGCGCCTCTGACCCCTCCGCTGTGACAGGACCAAAGGCGTCAGCCAGAG      383'
309    G  A  F  V  R  R  R  W  V  R  A  L  T  L  R  C  D  R  D  Q  R  R  Q  P  E      383
                           R

384'   TTTCCTAGAGTCACTCGTCGTCCAGCAGGACCACAGCCTGAGGCAGCCGCTTGAAGGCTCAGAGCACCAGGCTGCC    458'
384    F  P  R  V  T  R  P  A  G  P  T  A  *                                            458

459    GCCTGTGGTCCGGGACCTGTATGAGAATGCCAAGTACAACATCCTGAGAGACTTCTAGCGCTG                   533
534    GGCAACGGAGCAGGTGCACTGCATCCCAGCGCGACCTTCCCAGCGCGACCTTCACCTGCCCGCCCACCTTCA          608
609    GCACCCTCTCTGCACAGTCCAGGTTCTTTTGTCAGAACCCTGGGTAACCTGCTCTGCCCTTCACAT                683
684    ATCCAGACACTTCTCAGGCCAGGATGGGGGAGGTCAGACCGCCCCTTGGGTGAGAACCACAGGAGA                758
759    GTCTCAATAAAATGCTTCTGAAAGAAAAAAAAAAAAAA  798
```

FIG. 15

```
            1                                                                    40
Cathelin   . . . . Z L R Y R E A V L R A V D R L N E Q S S E A N L Y R L L E L D Q P P K A
Cap18      . . . Q D L T Y R E A V L R A V D D A F N O S S E A N L Y R L L S M D P O L E
P15h       I P H R R L R Y E V V A Q A L F Y N E G Q Q G Q P L F R L L E A T P P P S L 41                                                                    80
Cathelin   D E D P G T P K P V S F T V K E T V C P R P T R Q P P E L C D E K E . . Q K Q
Cap18      D A K P Y T P Q P V S F T V K E T E C P R T T W K L P E Q C D E K E D G L V K R
P15h       N S K S . . R I P L N F R I K E T V C I F T L D R Q P G N C A F R E G G E E R I 81                                                                    120
Cathelin   C V G T V T L N P S I H S L D I S C N E I Q S V . E S P E P T G L R K R L R K F R N K
Cap18      C V G T V T R Y Q A W D D F D I R C N R A Q .
P15h       C R G A F V R R V R R A L T L R C D R .

121                                              147
Cathelin   . I K E K L K K I G . . . . . . . . . . . . . . .
Cap18      . . . . . . . . . .
P15h       . D Q R R K I Q G L L P K L A P R T D Y . . . . . .
           . . . . . D Q R R Q P E F P R V T R P A G P T A
```

FIG. 17B actin

POLYPEPTIDES THAT POTENTIATE BACTERICIDAL/PERMEABILITY-INCREASING PROTEIN AND METHODS FOR TREATING BACTERIAL INFECTIONS

The United States government has rights to this invention by virtue of funding from the Department of Health and Human Services under Grant No. R37DK05472. This application is a continuation-in-part application of application Ser. No. 07/905,066 filed Jun. 24, 1992, now abandoned, which was a continuation-in-part application of application Ser. No. 07/767,551 filed Sep. 26, 1991 (now abandoned) which was a continuation of application Ser. No. 07/502,560 filed Mar. 30, 1990 (now abandoned).

FIELD OF THE INVENTION

This invention pertains to purified, isolated mammalian polypeptides having bactericidal/permeability-increasing protein ("BPI") potentiating activity, pharmaceutical formulations comprising the polypeptides, and methods for production and use of the. polypeptides and the formulations. The polypeptides of the invention are useful in combination with bactericidal/permeability-increasing proteins or biologically-active fragments thereof for treating gram-negative bacterial infections in mammals. In addition, the polypeptides of the invention alone or in combination with BPI neutralize lipopolysaccharides ("LPS") .

BACKGROUND OF THE INVENTION

Bactericidal/permeability-increasing protein is a 50 to 60 kilodalton (kDa) protein, isolated from the granules of mammalian polymorphonuclear leukocytes (hereafter "PMN"), blood cells that are essential in the immune defense against invading microorganisms in mammals. BPI is known to occur only in the myeloid series of blood cells, is produced at the promyelocytic/myelocytic stage of differentiation and is located in the primary granules in these cells.

BPI is a potent bactericidal agent active against a wide range of gram-negative bacterial species. It is highly effective and specific as a cytotoxic agent, i.e., 1–10 nM (0.05–0.5 micrograms) kills more than 90% of a population of $10^7$ sensitive (i.e. gram-negative) bacteria. 100-fold higher concentrations of BPI are non-toxic to other microorganisms or eukaryotic cells. All available evidence suggests that in the intact PMN as well as in crude leukocyte fractions, BPI is the principal oxygen-independent bactericidal agent active against gram-negative bacteria.

BPI isolated from both human and rabbit PMN has been purified to homogeneity. The molecular weight of human BPI is approximately 58,000 Daltons (58 kDa) and that of rabbit BPI is approximately 50 kDa. These two proteins have a similar amino acid composition and the amino acid sequence of the first 15 $NH_2$-terminal amino acid residues is also similar in rabbit and human BPI. Both proteins are highly basic, having an isoelectric point greater than 9.6. The entire amino acid sequence of human BPI has also been elucidated (as disclosed in copending commonly assigned U.S. patent application Ser. No. 228,035, filed Aug. 5, 1988, along with cDNA sequences encoding the BPI protein and cells transfected with the cDNA sequences).

The biological effects of BPI require attachment of the protein to the surface of susceptible gram-negative bacteria. Initial binding of BPI to target cells involves electrostatic interactions between the basic protein and the negatively charged sites on the lipopolysaccharides (LPS) in the bacterial outer membrane leading to an activation of bacterial enzymes that degrade phospholipids and peptidoglycans. The final stage of action is the actual killing of the bacteria by an as yet unknown mechanism. The closely similar amino acid composition and nearly identical bactericidal and membrane-perturbing properties of BPI purified from human and rabbit PMN suggest that this protein has been highly conserved during evolution and is an important member of the anti-bacterial arsenal of the mammalian PMN.

U.S. patent application Ser. No. 084,335 filed Aug. 6, 1987, now abandoned (in favor of its C-I-P, Ser. No. 228,035), discloses biologically active fragments of human and rabbit BPI proteins and methods to produce and use these proteins to combat infections caused by gram-negative bacteria. The fragments were approximately 25 kDa molecular weight and contained all of the biological activities of the entire protein.

Due to its potent bactericidal action against gram-negative bacteria and lack of cytotoxicity towards other microorganisms and eukaryotic cells, it is anticipated that BPI may be employed as a chemotherapeutic agent and/or as a model for the design of new antibiotic agents. It would be highly useful, therefore, to find an agent which potentiates or enhances the effectiveness of BPI against gram-negative bacteria, alone or in combination with other chemotherapeutic agents and/or antibiotics in killing gram-negative bacteria thereby allowing the use of lower effective amounts of BPI.

OBJECTS OF TEE INVENTION

It is an object of the present invention to provide mammalian polypeptides active in potentiating or enhancing the biological activity of bactericidal/permeability-increasing protein and methods for obtaining and purifying such polypeptides.

Another object of the present invention is to provide a method for purifying mammalian BPI proteins (synthetic or natural).

Yet another object of this invention is to provide methods to potentiate BPI activity.

A still further object of this invention is to provide more efficient methods for treating gram-negative bacterial infections in mammals by administering BPI proteins as chemotherapeutic or antimicrobial agents in conjunction with one or more polypeptides potentiating BPI.

Another object of this invention is to provide agents effective in neutralizing lipopolysaccharides.

These and other objects of the present invention will be apparent to those of ordinary skill in the art in light of the present description, claims and drawings.

SUMMARY OF THE INVENTION

The present invention is directed to mammalian polypeptides having bactericidal/permeability-increasing protein potentiating activity. These active polypeptides have been isolated and purified from crude acid extracts obtained from mammalian polymorphonuclear cells. Use of the BPI holoprotein (or biologically-active fragments thereof) in treating gram-negative bacterial infections in mammals is more effective in the presence of the polypeptides of this invention.

Another aspect of the present invention provides a method for purifying these polypeptides.

Another aspect of the present invention provides a method for purifying mammalian bactericidal/permeability-increasing proteins.

In yet another aspect, the present invention provides a method for treating infections caused by gram-negative bacteria in a mammal comprising administration to a mammal in need of such treatment an amount of an agent selected from the group consisting of bactericidal/permeability-increasing proteins and biologically-active fragments thereof in the presence of a BPI-potentiating polypeptide in an amount sufficient to potentiate or enhance the activity of BPI.

A further aspect of the present invention provides a pharmaceutical formulation for treating infections caused by gram-negative bacteria comprising (a) an amount of an agent selected from the group consisting of a bactericidal/permeability-increasing proteins and biologically-active fragments thereof, and (b) an amount of a BPI-potentiating mammalian polypeptide having bactericidal/permeability-increasing protein potentiating activity, the combined amounts of (a) and (b) together being more effective in killing said bacteria than the amount of (a) alone.

A still further aspect of the present invention provides a method for increasing the permeability of gram-negative bacteria to antibiotics by exposing said bacteria to (a) an amount of an agent selected from the group consisting of a mammalian bactericidal/permeability-increasing protein and biologically-active fragments thereof, (b) an amount of a mammalian polypeptide having bactericidal/permeability-increasing protein potentiating activity, the combined amounts of (a) and (b) together being more effective in increasing said permeability than the amount of (a) alone.

Another aspect of the invention is directed to compositions and methods for neutralizing lipopolysaccharides ("LPS") comprising exposing said LPS to the presence of the BIP-potentiating agents of the present invention, alone or in combination with BPI itself or active fragments of BPI.

BRIEF DESCRIPTION OF TEE FIGURES

FIG. 14 is a chart depicting the nucleotide and deduced amino acid sequence of the p15R and p15H cDNA'S of the present invention.

FIG. 15 is a chart showing a sequence comparison of p15H, catbelin and CAP-18.

DETAILED DESCRIPTION OF TEE INVENTION

All literature references, patent applications and patents cited in this specification are hereby incorporated by reference in their entirety.

"BPI holoprotein" is defined herein to mean the entire mammalian BPI molecule (58 kDa, for human BPI and 50 kDa for rabbit BPI).

As used herein, "biologically-active fragments of BPI" are fragments of the BPI molecule containing the biological activity of the BPI holoproteins as disclosed in copending U.S. patent application Ser. No. 228,035. Specific biologically-active BPI fragments of human and rabbit BPI disclosed in said application have molecular weights of approximately 25 kDa.

Mammalian polypeptides having BPI potentiating activity have now been discovered. Two such mammalian polypeptides, each having an apparent m.w. of 15,000 daltons, can be isolated as two closely similar isoforms. These two isoforms (15KA and 15KB) have been isolated from acid extracts of mammalian PMN, the same source as the BPI protein. These 15K polypeptides by themselves have no growth-inhibitory or other antibacterial activity against gram-negative bacteria although they do potentiate these activities of BPI.

Figure 1:
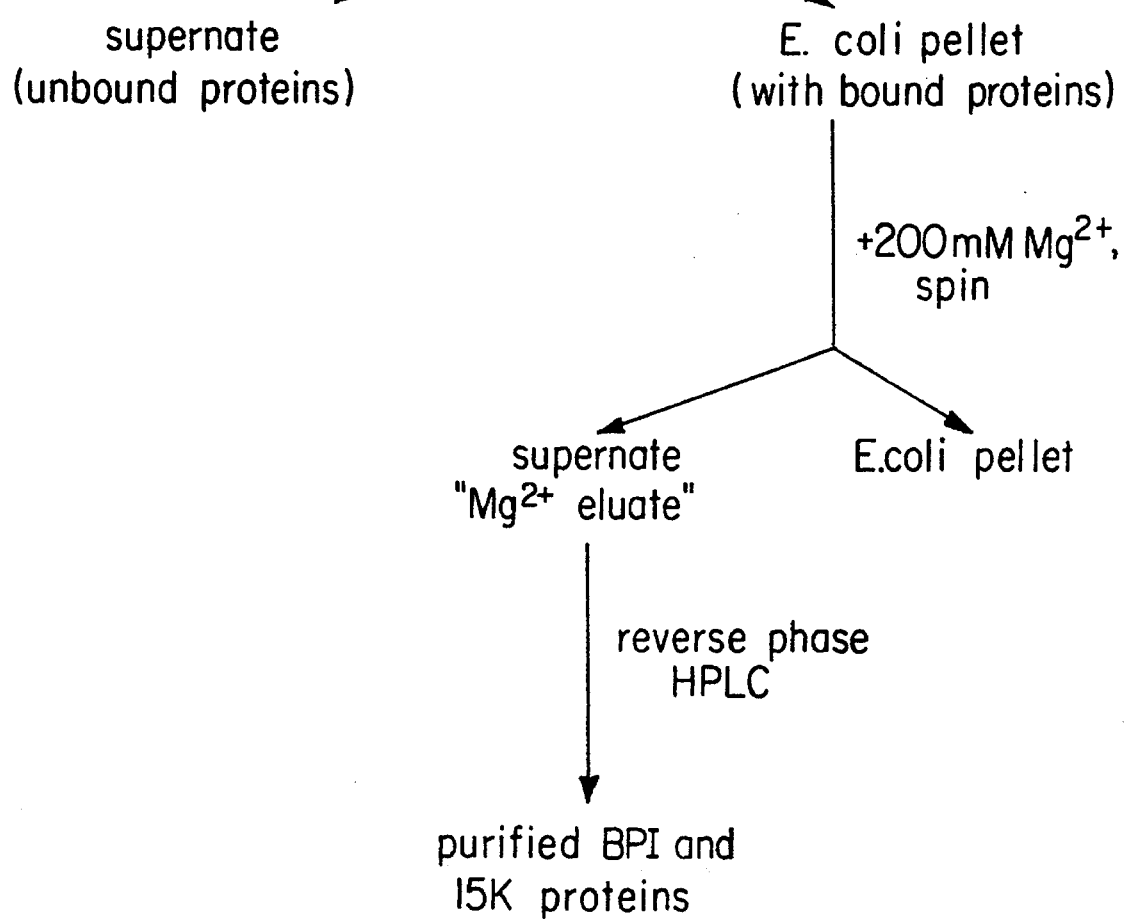
FIG. 1 is an outline depicting a procedure for isolating two 15 kDa polypeptides in accordance with the invention, i.e., two polypeptides having BPI potentiating activity, and also a procedure for purifying BPI protein from crude preparations thereof, here rabbit PMN acid extracts.

The term "BPI potentiating activity" as used herein refers to an increase in or potentiation of the biological activity of BPI or its biologically-active fragments in the effective growth-inhibition and treatment of gram-negative bacterial infections in mammals. Thus, the 15K mammalian polypeptides allow the use of smaller quantities of the BPI holoprotein (or of biologically-active fragments of BPI) or increase the efficacy of given amounts of BPI or fragments. By a unique method depicted in the outline shown in FIG. 1, these 15K mammalian polypeptides can be isolated and purified; bactericidal/permeability-increasing (BPI) proteins can also be purified using this scheme.

"Neutralizing LPS" as used herein is defined as inhibiting the deleterious biological effects of gram negative bacterial lipopolysaccharide such as Tumor Necrosis factor (TNF) release and/or production or activation of inflammatory substances such as Interleukin-1 (IL-1), Interleukin-6 (IL-6) or Interleukin-8 (IL-8) and similar endogenous mediators of septic shock, as is well known in the art. Any reduction or inhibition of the production and/or activation of these cytokines pursuant to treatment as set forth in this application is within the scope of the present invention.

In more detail, these BPI-potentiating peptides can be purified as follows: A suitable biological sample is isolated from a mammalian source, e.g., a crude polymorphonuclear leukocyte (PMN) acid extract which may be obtained from mammalian blood as described in copending U.S. patent application Ser. No. 228,035.

The isolated crude mammalian PMN acid extract, is then mixed with a culture of gram-negative bacteria, e.g., *Escherichia coli*. The procedure is conducted under conditions that promote binding of the desired 15K mammalian polypeptides of the present invention to the bacterial envelope. A particularly useful strain of bacteria for use in accordance with the present invention is the *E. coli* strain designated J5 (Mannion, B. A. et al., *J. Immunol.* 142: 2807–2812, 1989). Alternatively, other commonly used laboratory strains of *E. coli* or *Salmonella typhimurium* (as disclosed in Elsbach, P. et al., *J. Biol. Chem.* 254: 11000–11009, 1979; Weiss, J. et al., *J. Clin. Invest.* 65: 619–629, 1980; Weiss, J. et al., *Infect. Immun.* 38: 1149–1153, 1982; Weiss, J. et al., *J. Clin. Invest.* 71: 540–549, 1983) may be employed in practicing the present invention.

These 15K mammalian polypeptides can be bound to gram-negative bacteria by incubating acid extracts obtained from PMN with the bacteria in a buffer-modified medium having a pH between about 4.0 and about 8.0 preferably about 7.4, and containing a biologically-acceptable binding salt concentration ranging between about 2 mM and about 200 mM, preferably of about 150 mM and at temperatures of between about 20° C. and about 40° C., preferably about 37° C., for between about 5 minutes and about 30 minutes, preferably about 15 minutes. The ratio of acid extract to bacteria is broadly between about 20 micrograms to 1 milligram of protein extract to about $10^8$ bacteria.

Non-limiting examples of biologically-acceptable binding salts for use in the present invention include NaCl and KCl and other sodium and potassium containing monovalent salts such as sodium acetate.

Following the incubation period, the mixture is centrifuged at approximately 5000×g for about 10 minutes. After centrifugation, the supernatant containing unbound protein is removed, leaving a pellet containing the bacteria with the 15K mammalian polypeptides bound to the bacteria.

The pellet is next resuspended in a buffered solution that has an effective concentration of elution salts to elute the 15K mammalian polypeptides and the BPI protein. Nonlimiting examples of suitable elution salts for use in this step include $MgCl_2$, or $CaCl_2$ and other divalent cations such as $MnCl_2$. $MgCl_2$ or $CaCl_2$ are preferred because these salts have been shown to be the most effective in displacing bound materials from the bacteria in this method. Concentrations ranging between about 100 mM and about 500 mM, and preferably 200 mM have been found suitable to elute the 15K mammalian polypeptides. Centrifugation at approximately 7500×g for about 10 minutes yields a bacterial pellet and a supernatant or salt eluate, the latter of which contains the 15K mammalian polypeptides. Because the BPI holoprotein is also obtained by this procedure (see below), in order to isolate the 15K mammalian polypeptides of the present invention in homogeneous form, further fractionation is required. Preferably, the eluate is further fractionated as described below to yield two isolated, homogeneous proteins.

Reverse phase high performance liquid chromatography (RPHPLC) or any other conventional ion exchange and/or gel filtration procedure such as molecular sieve chromatography known to be useful for purifying biologically active proteins may be performed on the salt eluate. RPHPLC using a Vydac $C_4$ column (the Separations Group, Hesperia, Calif.) as described in Mannion, et al., supra, and Ooi, C. E. et al., *J. Biol. Chem.* 262: 14891–14894, 1987 and in Examples 1 and 6 below is preferred. Fractions are collected from the RPHPLC and recovered, at least one fraction is enriched in the 15K mammalian polypeptides.

The 15K mammalian polypeptides can be further resolved at this point into two closely related isoforms, 15KA and 15KB, by further fractionation on RPHPLC as shown in Example 6 below and each can be recovered in a homogeneous form, i.e. purified, isolated 15KA and 15kB. Alternatively, a mixture of 15KA and 15KB can be resolved, e.g., by cation exchange chromatography as shown below in Example 6 using, for example, a Mono S Column (Pharmacia Fine Chemicals, Piscataway, N.J.) or any other suitable column such as CM-Sephadex (Pharmacia) when using cation exchange cchromatography to separate 15KA from 15KB.

Although 15KA and 15KB have identical N-terminal amino acid sequences, the mammalian polypeptides can be distinguished from each other by their biological effects. Isolated 15KA strongly (6–10 fold) potentiates the antibacterial effects mediated by BPI whereas 15KB more weakly (up to 3-fold) potentiates these effects. A 1:3 mixture of 15KA+15KB moderately (3–6 fold) potentiates the effects of BPI. Any potentiation of the biological effects of BPI on gram negative bacterial growth (or the products thereof) by the 15K mammalian polypeptides of the present invention is within the scope of the present invention. In addition both 15K isoforms inhibit the late antibacterial effects of BPI.

Although the 15K mammalian polypeptides of the present invention have been isolated and purified from rabbit PMN, it is believed that other mammalian PMN (especially those derived from human donors) will also contain these activities. In like manner to the BPI holoproteins, it is believed that BPI-potentiating mammalian polypeptides will be present in the myeloid series of blood cells. Alternatively, BPI-potentiating polypeptides according to the invention may be synthesized after elucidation of the sequence of the naturally-occurring polypeptides (or active fragments or analogs thereof) using. sequencing and recombinant techniques now well known in the art.

In addition, the present invention provides a method for purifying mammalian BPI holoproteins and/or biologically active fragments of said holoproteins. The present inventors have discovered that the same method used to isolate the 15K mammalian polypeptides can also be used to purify BPI holoproteins and/or biologically-active fragments thereof. The method is relatively inexpensive, rapid and leads to a quantitative recovery of the BPI proteins and/or biologically active fragments in a homogeneous form, i.e. no other stainable bands are seen on a SDS-PAGE gel of the purified materials after RPHPLC. The method can be practiced on both a small (analytical) and a large preparative scale. When practicing the method on a large scale, the ratio amounts of extract to gram negative bacteria should be 20 micrograms to 1 mg per $10^8$ bacteria for purifying the 15K mammalian polypeptides. The method comprises the steps of (i) incubating a sample comprising said mammalian BPI protein and gram-negative bacteria under conditions sufficient to bind said BPI protein to said bacteria; (ii) removing non-bound material; and (iii) eluting and recovering the BPI protein from the bacteria. The same steps and conditions described above for purifying the 15K mammalian polypeptides are also used to purify the BPI holoprotein and biologically-active fragments thereof. The eluate may be then further purified by, for example, RPHPLC, following steps wellknown in the art.

Figure 2:
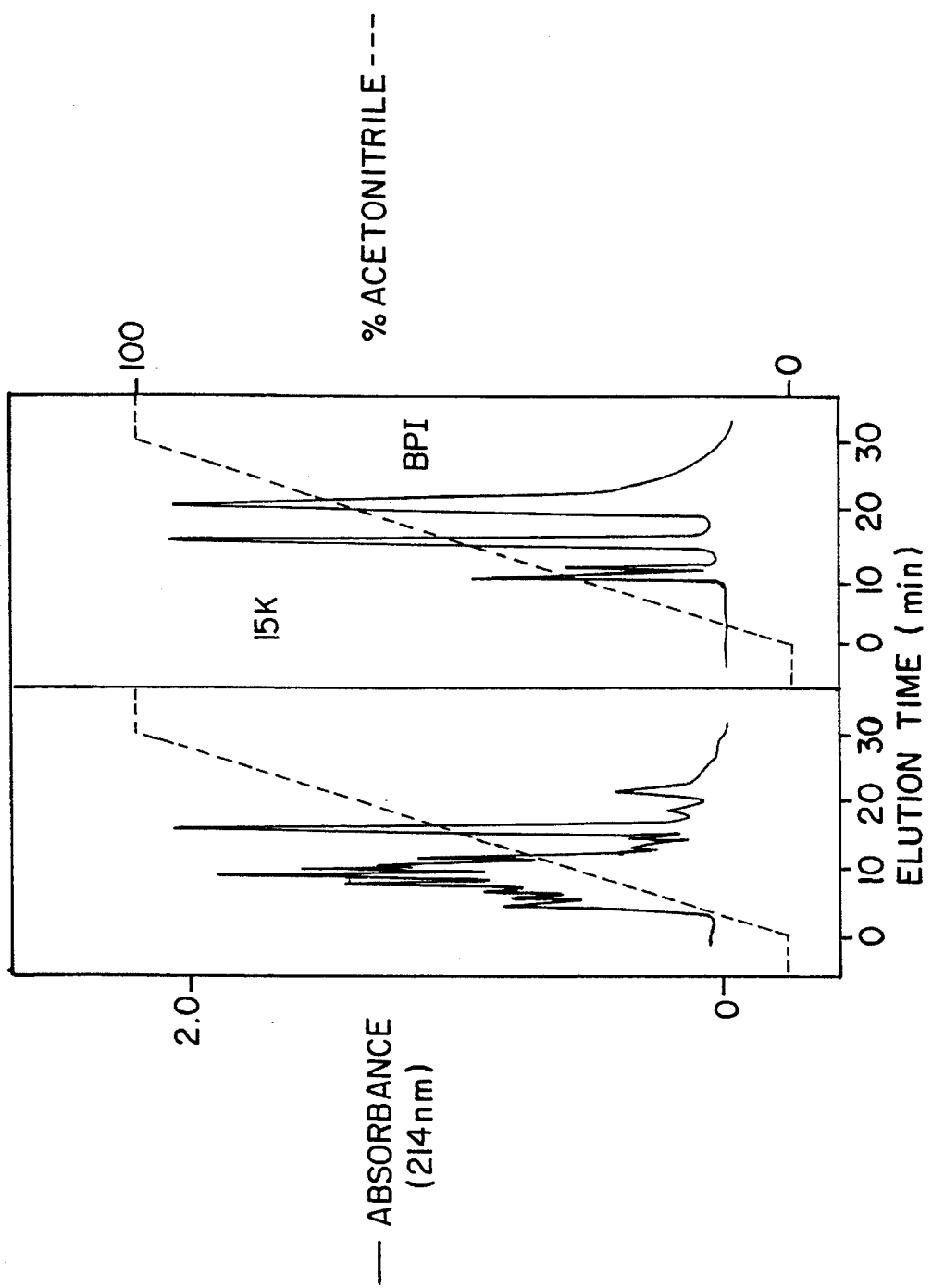
FIG. 2 depicts the elution profile of BPI and two 15K polypeptides of the present invention from a reverse phase HPLC of crude rabbit PMN acid extracts.

FIG. 2 illustrates the protein absorbency (and % acetonitrile) over various elution times (0 to 30 minutes) for a crude rabbit PMN extract (left panel) and a salt eluate (right panel) obtained pursuant to the method of the present invention. As can be seen in FIG. 2, under the conditions described above, the 15K mammalian polypeptides and the BPI holoprotein eluted in separate fractions from RPHPLC, i.e. the 15K mammalian polypeptides eluted at about 15 minutes and the BPI holoprotein eluted at about 20 minutes. After RPHPLC the BPI holoprotein was homogeneous but the 15K mammalian polypeptides were present in two closely related isoforms which can be separated as described above and in Example 6 below.

Figure 3:
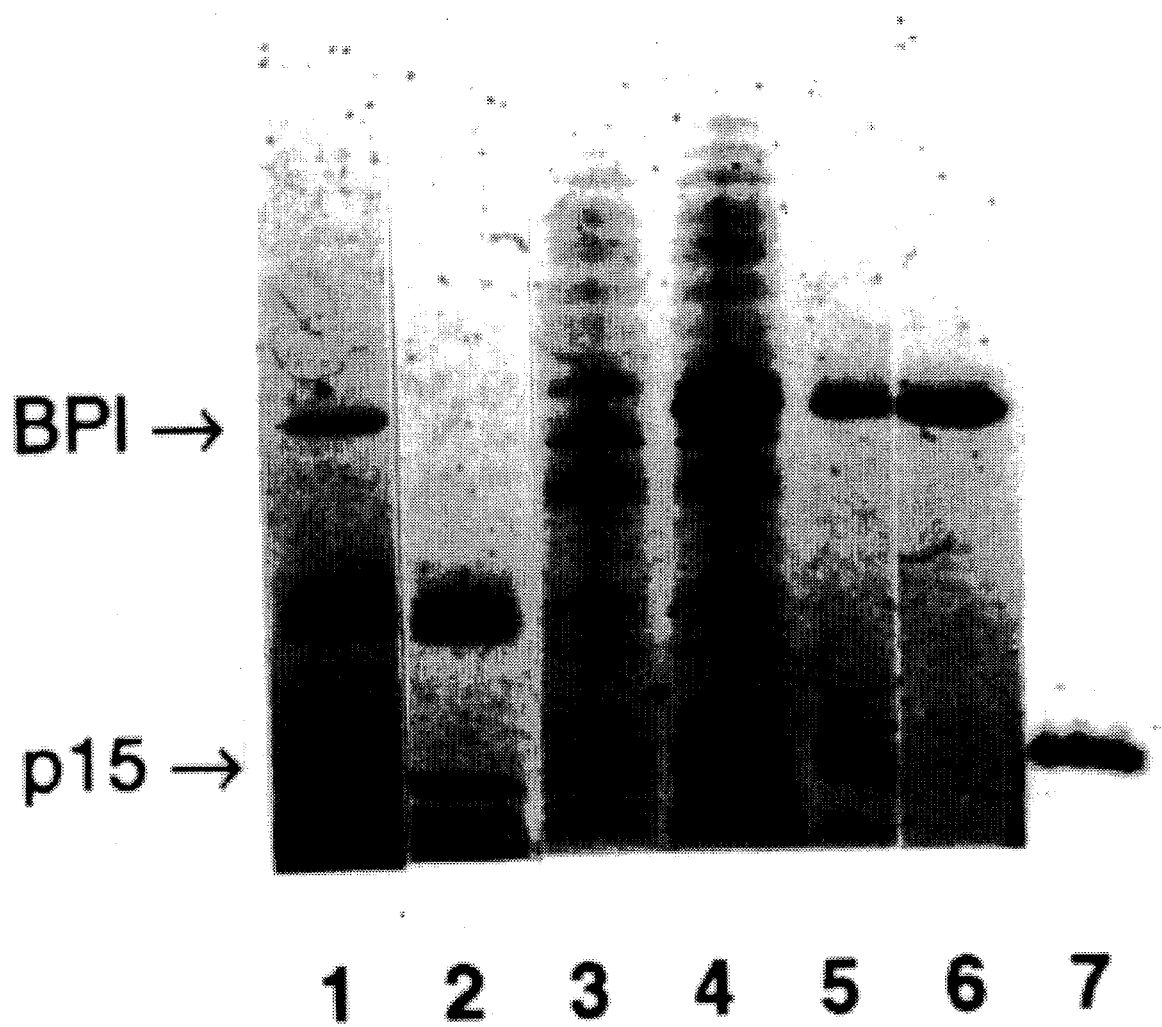
FIG. 3 is a photograph of a stained SDS-PAGE gel showing isolation of two 15K polypeptides according to the present invention and isolation of the BPI protein.

SDS-PAGE analysis using the PhastGel® System (Pharmacia, Inc., Piscataway, N.J.) with either an 8–25% or an 10–15% polyacrylamide gradient gel was performed on the material purified as above and the protein bands visualized by Coomassie blue staining well-known in the art. Analysis from the SDSPAGE patterns as shown in FIG. 3 indicated that an estimated quantity of 50–100 micrograms of the 15K mammalian polypeptides of the present invention was obtained per $10^8$ cell equivalents of crude extract. This amount is approximately equal to the amount of the BPI protein recovered from the same amount of extract.

Thus, two BPI-potentiating mammalian polypeptides have been purified to homogeneity and characterized. The amino acid composition of the two 15K mammalian polypeptides, isolated and purified using the method in Example 6 below, is set forth below. Methods within the skill of the art can be used to identify fragments of BPI-potentiating polypeptides and analogs thereof having the same activity as well as additional naturally occurring polypeptides with BPI-potentiating (and LPSbinding) properties. The invention is thus not limited to the two 15K polypeptides described in detail herein.

| AMINO ACID | (MOL %) | |
| --- | --- | --- |
| | 15 KA | 15 KB |
| Asx | 6.1 | 6.1 |
| Glx | 14.4 | 14.0 |
| Ser | 2.6 | 3.4 |
| Gly | 6.3 | 6.1 |
| His | 0.8 | 1.1 |
| Arg | 16.5 | 15.6 |
| Thr | 4.1 | 4.1 |
| Ala | 6.6 | 6.6 |
| Pro | 14.1 | 14.4 |
| Tyr | 1.9 | 2.2 |
| Val | 4.8 | 4.7 |
| Met | 0.2 | 0.4 |
| Cys | ND | ND |
| Ile | 4.1 | 4.1 |
| Leu | 8.3 | 8.2 |
| Phe | 5.6 | 4.7 |
| Lys | 3.2 | 3.6 |

(ND = not determined)

The $NH_2$-terminal amino acid sequences of the 15K mammalian polypeptides have been determined as described in Example 2 below and are identical in their first 20 amino acid residues: 15KA: Ile—Pro—His—Arg—Arg—Leu—Arg—Tyr—Glu—Glu—Val— Val—Ala—Gln—Ala—Leu—Gln—Phe—Tyr—Asn. 15KB: Ile—Pro—His—Arg—Arg— Leu—Arg—Tyr—Glu—Glu—Val—Val—Ala—Gln—Ala—Leu—Gln—phe—Tyr—Asn. These sequences are distinct from that of rabbit or human BPI.

In addition to these structural and molecular characteristics, the biological activities and properties of the 15K mammalian polypeptides have also been studied.

Figure 4:
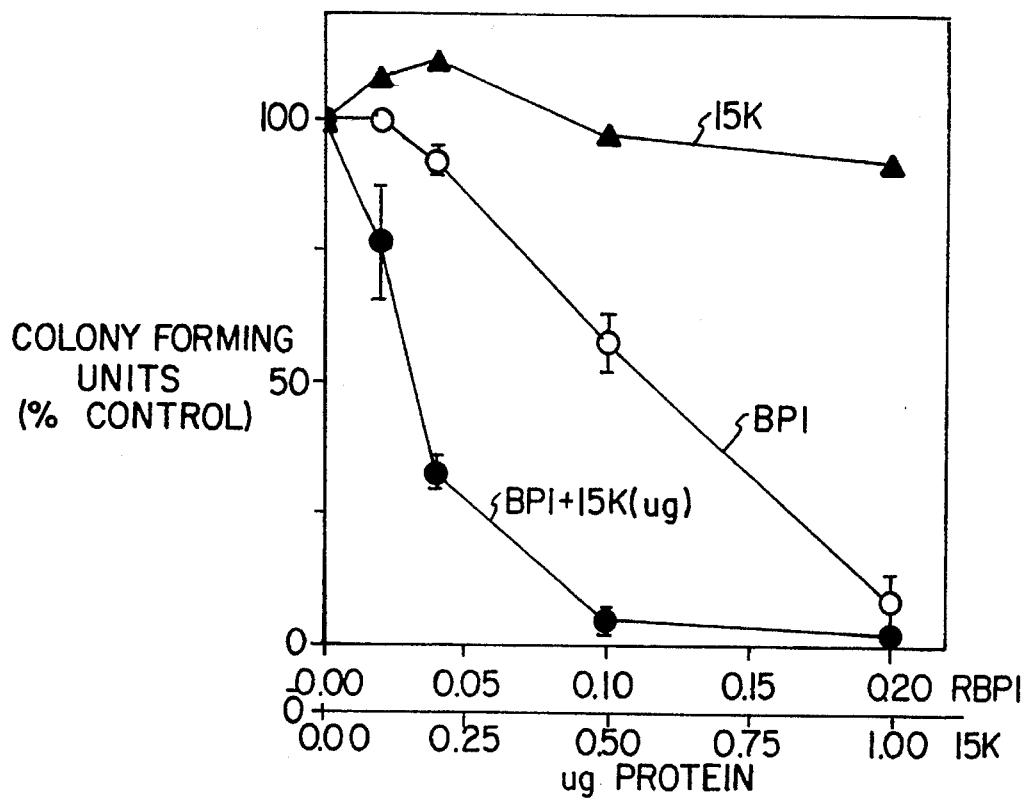
FIG. 4 is a graph depicting the BPI potentiating activity of two 15K BPI-potentiating polypeptides in inhibiting colony formation of E. coli J5.
Figure 5:
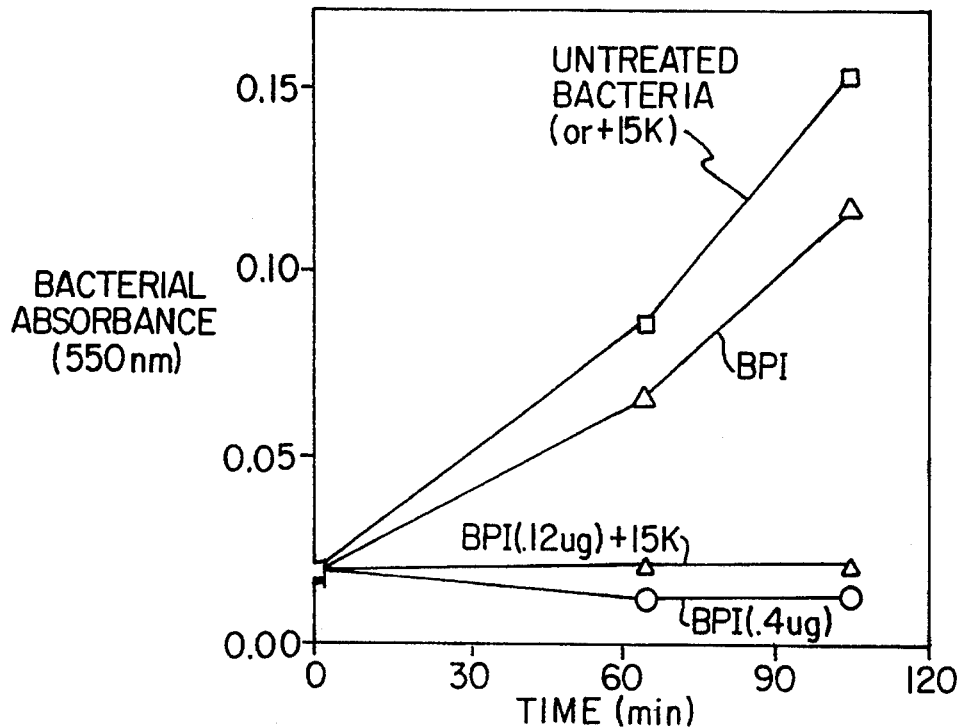
FIG. 5 is a graph illustrating BPI potentiating activity of two 15K polypeptides according to the present invention in arresting growth of gram-negative bacteria in liquid medium.
Figure 6:
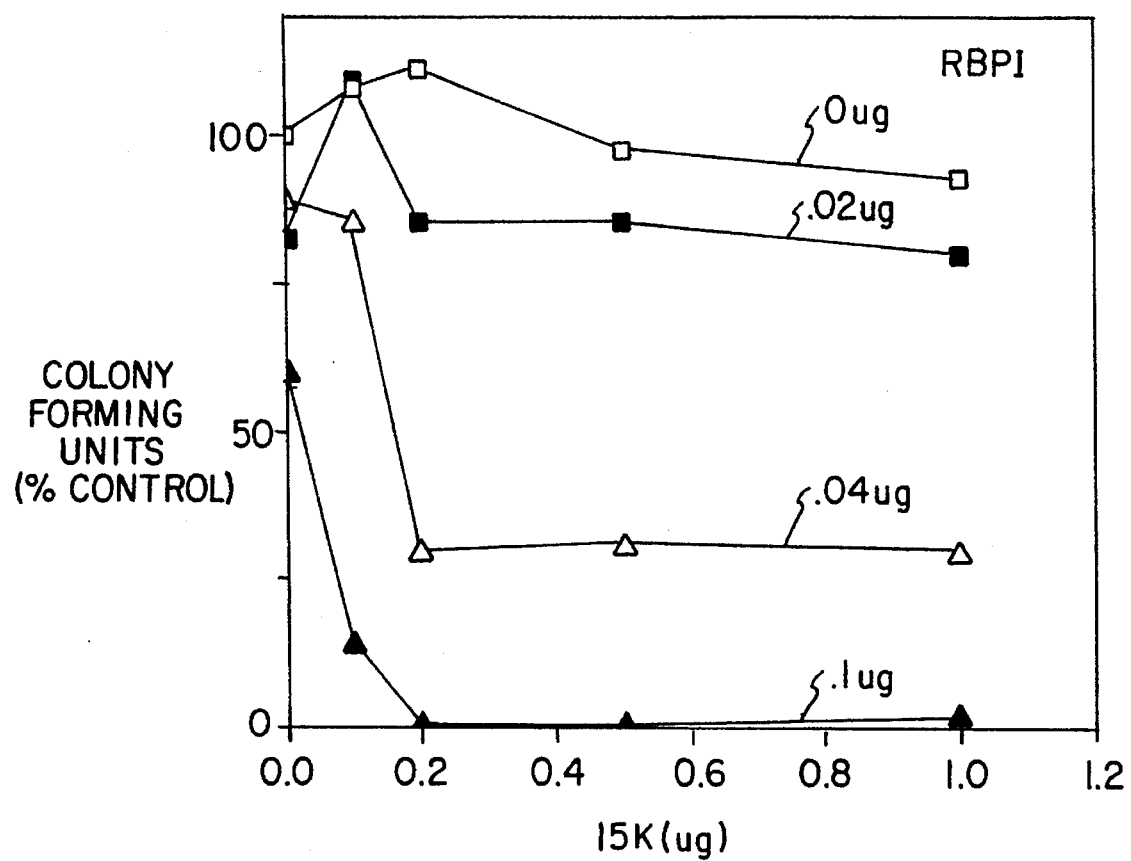
FIG. 6 is a graph depicting the growth inhibition dose curve for two 15K polypeptides according to the invention and a mammalian, i.e., rabbit, BPI protein.
Figure 7A:
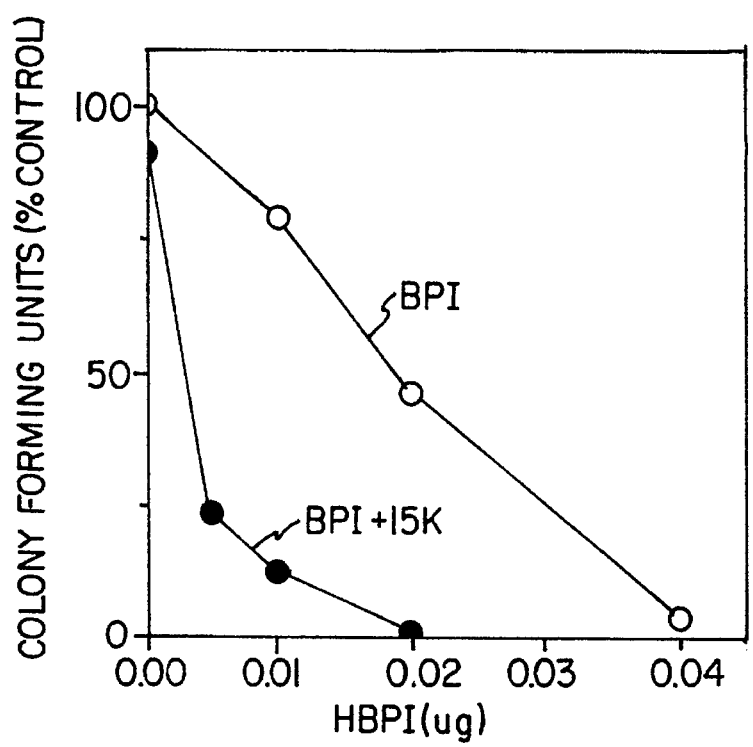
FIG. 7 is a series of graphs comparing the biological activities, i.e., growth-inhibiting activities on E. coli J5 using the two 15K polypeptides alone, or in combination with other killing agents: (A) human BPI protein (holoprotein); (B) 25 kDa fragment of human BPI; (C) Polymyxin B; and (D) normal human serum.
Figure 7B:
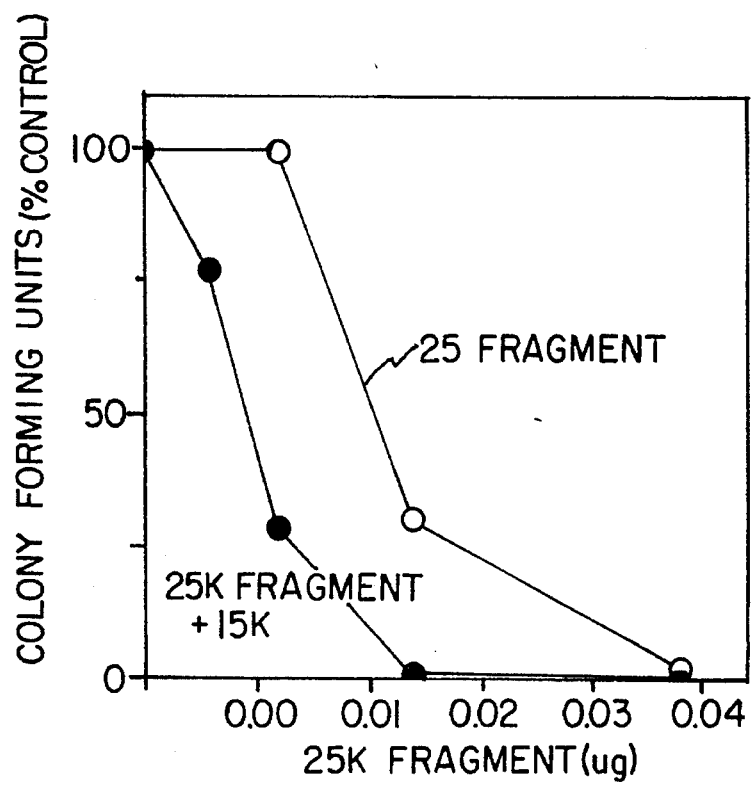
Figure 7C:
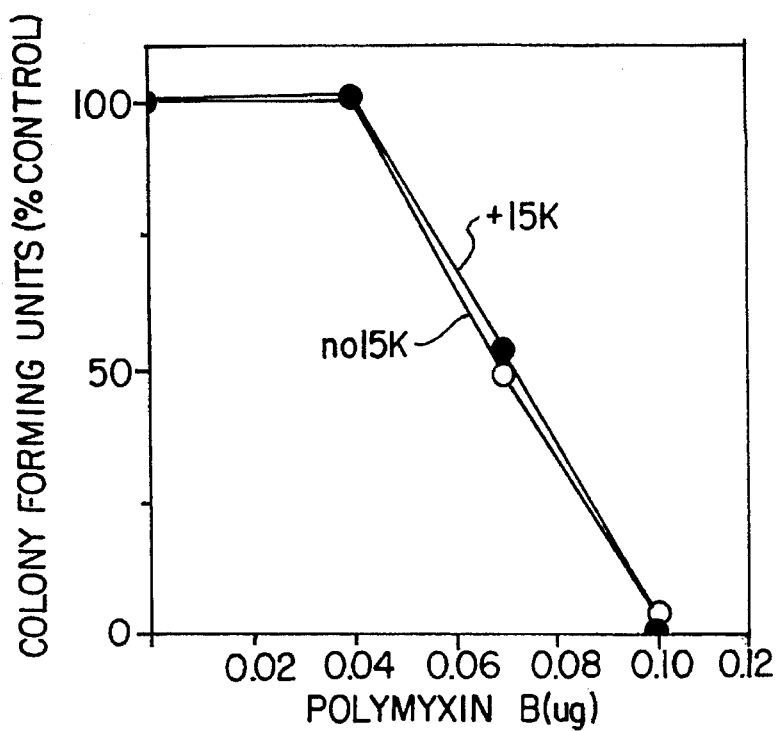
Figure 7D:
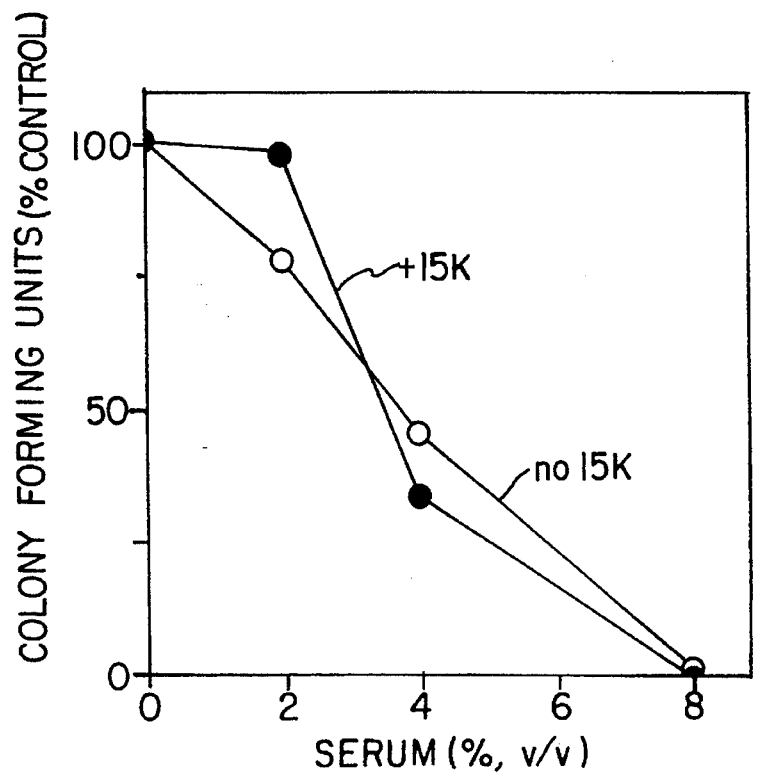

Growth-inhibition of gram-negative bacteria, e.g., *E. coli* J5 was investigated (by measuring the arrest of colony formation and growth arrest in liquid medium) to determine the biological activity of the two 15K mammalian polypeptides according to the present invention. The specific details of these studies are set forth below in Example 3 and the results are illustrated in FIGS. 4, 5 and 6. It has been discovered that the 15K mammalian polypeptides alone had no antibacterial activity against gram-negative bacteria in the absence of human BPI or of at least one of its biologically-active fragments. When combined with BPI, the 15K mammalian polypeptides were found to reduce (by up to 10-fold when using the isolated 15KA isoform) the quantity of BPI needed to afford maximal gram-negative bacterial growth inhibition as shown in Example 6 below. Thus, the 15K mammalian polypeptides of this invention have been shown to potentiate BPI protein activity against gram-negative bacteria. The 15KA mammalian polypeptide isoform strongly potentiated (6–8 fold) the antibacterial effects of BPI, a mixture of 15KA+15KB mammalian polypeptides moderately (3–6-fold) potentiated BPI antibacterial activity, and the 15KB mammalian polypeptide weakly (up to 3-fold) potentiated this effect. Therefore, use of 15KA in combination with BPI to treat infections caused by gram negative bacteria is a particularly preferred embodiment of the present invention. Alternatively, a combination of 15KA and 15KB, or larger amounts of 15KB can also be used.

As described in Example 4 below and as illustrated in FIG. 6, a maximal BPI enhancing or potentiating effect was obtained with about 0.2 micrograms (70 nM) of 15K mammalian polypeptides (which in this experiment happened to be a mixture of 15KA and 15KB) per $10^7$ bacteria and from 0.01 to 0.04 micrograms of BPI. This combination completely inhibited bacterial growth.

In addition, as shown below in Example 4, other agents have been tested to determine if the 15K mammalian polypeptides would potentiate growth inhibition of gram-negative bacteria produced by such agents. The human BPI protein (the holoprotein), a 25K biologically active fragment of the human BPI protein, polymyxin B (a gram-negative-specific antibacterial antibiotic) and normal human serum were all tested for growth inhibition in the presence and absence of the 15K mammalian polypeptides (used in a 1:3 ratio of 15KA: 15KB) of the present invention. The results of these experiments showed that the 15K mammalian polypeptides potentiated the growth inhibition of gram-negative bacteria mediated by human BPI and/or the biologically active 25K fragment of human BPI but had no effect on polymyxin- or serum-mediated killing of such bacteria. Although the rabbit 15K polypeptides potentiated the activity of human BPI (or the biologically-active fragment thereof), the use of the same species of 15K mammalian polypeptides and BPI protein is preferred.

The 15K mammalian polypeptides have also been characterized in terms of their potentiation of the effect of BPI on the gram-negative bacterial envelope. These mammalian polypeptides were found to potentiate the effects of BPI protein on the gram-negative bacterial outer membrane, evident by an increased permeability of the bacterial membrane to the normally impermeant antibiotic, actinomycin D, and activation of phospholipid degradation.

In like manner to the BPI protein, the 15K mammalian polypeptides preferentially bind to $E.$ $coli$ when exposed to crude acid extracts of whole PMN. Unlike the BPI protein, however, the 15K mammalian polypeptide bind to $E.$ $coli$ without recognizable functional or biological effects on such bacteria. In addition, the 15K mammalian polypeptide reduced the effective anti-bacterial BPI dose by about 5–10-fold. In other words, by employing the 15K mammalian polypeptides lower amounts of BPI or its biologically-active fragments may be employed to kill gram-negative bacteria.

The present inventors have found that saturation binding of BPI to gram-negative bacteria is reached at 2.2 micrograms of BPI protein per $10^7$ bacteria. Binding analysis also showed a single, high affinity binding site on the bacteria for BPI with an apparent affinity constant (K) of 23 nM and that gram-negative bacteria contain approximately 2.2 million BPI binding sites per bacterium. It should be noted that the BPI proteins (both holoproteins and biologically active fragments thereof.) have greater binding affinities for the envelope of gram negative bacteria (polysacchorides) than any other proteins present in the extract. The ratio of binding affinities is BPI>15K mammalian polypeptides more than other cationic proteins of the PMN.

The 15K mammalian polypeptide of the present invention can be utilized in conjunction with BPI holoproteins and/or biologically-active fragments thereof for treating mammals suffering from diseases caused by gram-negative bacteria such as bacteremia or sepsis (the presence of bacteria in the bloodstream) or the toxic effects of gram negative bacterial infections. The mammalian polypeptides of the present invention would be particularly useful in combination with BPI in treating the toxic effects of LPS (endotoxin) in such diseases as gram-negative septic shock (described by Marra, M. N. et al. (*J. Immunol.* 144: 662–666, 1990), as described below.

Because both BPI or the 15K mammalian polypeptides have high affinity for lipopolysaccharides (endotoxins) in the outer envelope of gram-negative bacteria the administration to mammals of the combination of BPI (or biologically active fragments thereof) and the 15K mammalian polypeptides of the present invention offers two anticipated benefits in gram-negative bacterial infection and septic shock:

(1) arresting the proliferation of the infectious agents, and/or (2) neutralizing the LPS (endotoxins) that initiate the life-threatening consequences (septic shock) of gram-negative bacterial infections.

Non-limiting examples of gram-negative bacterial infections which can be treated using the method of the present invention include those caused by *Escherichia coli,* various species of Salmonella, Klebsiella or Pseudomonas. The 15K mammalian polypeptides of the present invention can also be advantageously co-administered (with the BPI holoprotein and/or biologically-active fragments thereof) with any antibiotic (active against gram-negative bacteria), immune system cells (such as T-cells or antibodies, or the like), effective against gram-negative bacteria as disclosed in U.S. patent application Ser. No. 228,035.

BPI proteins and biologically-active fragments thereof for use in the present invention can be isolated and purified using the procedures described above or those set forth in assignee's co-pending U.S. patent application Ser. No. 228,035. In addition, using the sequence information for the human BPI holoproteins and/or biologically-active fragments thereof disclosed in U.S. patent application Ser. No. 228,035, the human BPI proteins can be obtained after introduction of suitable DNA and synthesis by transfected eukaryotic (e.g. mammalian or yeast) or prokaryotic cells using techniques disclosed therein.

Therefore, in accordance with the present invention, a method is provided for treating gram-negative bacterial infections in a mammal comprising administering to a mammal in need of such treatment of (a) an amount of an agent selected from the group consisting of a bactericidal/permeability-increasing protein and biologically-active fragments thereof; and (b) an amount of a mammalian polypeptide having bactericidal/permeability-increasing protein potentiating activity, the combined amounts of (a) and (b) together being effective to kill said gram-negative bacteria.

The amount of (a) said bactericidal/permeability-increasing protein or biologically active fragments thereof that is effective for killing 107 gram-negative bacteria/ml broadly ranges between about 0.1 micrograms and about 10 micrograms, preferably between about 1 microgram and about 5 micrograms of the holoprotein depending upon the sensitivity of different gram-negative bacterial species and strains, and assay conditions. The biologically-active BPI fragments are effective in killing gram-negative organisms when administered at levels that are 25 to 50% less than the amount of the BPI holoprotein with or without the 15K mammalian polypeptide of the present invention. The amount of (b) said mammalian polypeptide broadly ranges between about 0.1 micrograms and about 1.0 microgram, and preferably, between about 0.2 micrograms and 0.4 micrograms.

Preferably, the 15K polypeptides (either in a mixture of 1:3, 15KA to 15 KB or most preferably the isolated 15KA isoform) of the invention and/or BPI protein may be administered via the topical route (to treat gram-negative bacterial infections of the skin, open wounds, burns, etc.) and also by perfusion of body cavities, e.g. the urinary tract, the peritoneal cavity and the mammary gland. The 15K mammalian polypeptide and the BPI protein may also be administered parenterally to mammals afflicted with gram-negative bacterial infections (i.e. by intravenous, intramuscular, intraperitoneal, subcutaneous or intradermal route).

The 15K mammalian polypeptides of the present invention and BPI protein (or biologically active fragments thereof) may be administered sequentially or preferably substantially simultaneously. If the 15K mammalian polypeptides and the BPI protein and/or biologically active fragments thereof are administered sequentially, the 15K polypeptides of the present invention are preferably administered before (broadly within about 1 hour) the BPI protein.

Pharmaceutical formulations for treating mammals suffering from infections caused by gram-negative bacteria can be prepared with the 15K mammalian polypeptides (having bactericidal/permeability-increasing protein potentiating activity) of the present invention. Pharmaceutical formulations of the present invention useful in treating gram-negative bacterial infections comprise an effective amount for inhibiting the growth of gram-negative bacteria in mammals of the 15K mammalian polypeptides of the present invention (or pharmaceutically acceptable salts thereof) together with well-known pharmaceutically-acceptable carriers, diluents, fillers, salts and other materials well-known in the art depending on the dosage form utilized. For example, a preferred topical dosage form may comprise between about 100 micrograms and about 500 micrograms of the 15K mammalian polypeptides of the present invention and may be formulated in the same type of preparations used in well-known antibiotic creams (such as Silvadene, Marion Laboratories, Kansas City, Mo.; Terramycin, Pfipharmecs, New York, N.Y.; or Acromycin, Lederle Laboratories, Pearl River, N.Y.). A preferred parenteral dosage form may comprise a sterile isotonic saline solution containing between about 100 micrograms and about 500 micrograms of the 15K mammalian polypeptides of the present invention and one or more physiologically acceptable carriers or diluents. The parenteral dosage form should have a pH broadly between about pH 7 and about pH 8 and preferably pH 7.4. Additional pharmaceutically acceptable salts or carriers useful in the invention include isotonic saline, physiologically buffered saline solutions, dextrose, lysozyme or a combination of any of the foregoing. The formulations may also comprise an effective amount (as described above) of the BPI holoprotein and/or biologically-active fragments thereof.

It will be appreciated that the unit content of active ingredients contained in an individual dose of each dosage form need not in itself constitute an effective amount for killing or inhibiting the growth of gram-negative organisms since the necessary effective amount can be reached by administration of a plurality of such dosage forms.

The present invention also provides a method of inhibiting the growth of gram-negative bacteria comprising exposing said bacteria to (a) a predetermined amount of an agent selected from the group consisting of a bactericidal/permeability-increasing protein and biologically-active fragments thereof, and (b) an amount of a mammalian polypeptide having bactericidal/permeability-increasing protein potentiating activity, the combined amounts of (a) and (b) together being effective to inhibit the growth of said bacteria as disclosed above.

The present invention further provides a method of increasing the permeability of gram-negative bacteria to antibiotics comprising exposing said bacteria to (a) an amount of a mammalian polypeptide having bactericidal/permeability-increasing protein potentiating activity and (b) a predetermined amount of an agent selected from the group consisting of a mammalian bactericidal/permeability-increasing protein and biologically-active fragments thereof, said combined amounts of (a) and (b) together being effective to increase the permeability of gram-negative bacteria and an effective amount of an antibiotic. Suitable antibiotics for use in this embodiment of the present invention include but are not limited to Penicillin-G (available from E. R. Squibb and Sons, Princeton), cephalosporins (available from Eli Lilly and Co., Indianapolis, Ind.) and especially hydrophobic antibiotics such as rifampicin (available as RIFAMPIN, CIBA Pharmaceuticals, Summit, N.J.) and hydrophobic penicillins such as Penicillin-V Benzanthine (Lederle Laboratories, Inc., Pearl River, N.Y.). The increased permeability of gram-negative bacteria after treatment with BPI and the 15K mammalian polypeptides of the present invention is expected to enhance the effectiveness of such hydrophobic antibiotics (and other antibiotics) which cannot otherwise easily enter gram-negative organims to exert their antibiotic effects.

The present invention is described below in specific working examples which are intended to illustrate the invention without limiting its scope.

EXAMPLE 1

Isolation and Purification of 15K Mammalian Popypeptides and BIP Protein

A rabbit PMN acid extract was obtained as described in U.S. patent application Ser. No. 228,035 filed Aug. 5, 1988. Suspensions were prepared containing $5 \times 10^8$ E. coli J5/ml and 5 milligrams of PMN extract per ml of buffered (Tris/HCl, pH 7.4) normal saline. The mixture was incubated at 37° C.. for 15 minutes.

Following incubation, the mixture was centrifuged (5000 ×g) for 10 minutes and the supernatant (containing unbound proteins) was removed, washed once with normal saline, and set aside for later SDS-PAGE analysis. The E. coli pellet with bound proteins was washed twice with the same buffer and resuspended in 0.1 volumes of a buffered (pH 4.0) 200 mM $MgCl_2$ solution and centrifuged (5000×g) for 10 minutes. The supernatant (Mg2+) eluate was removed, dialyzed against 200 mm $MgCl_2$ buffer (pH 4.0) and purified by RPHPLC using a Vydac C4 column (The Separation Group, Hesperia, Calif.) in a gradient of acetonitrile from 0%–95% containing 0.1% trifluoroacetic acid (TFA developed) for 0 minutes. Fractions were collected from RPHPLC and analyzed spectrophotometrically for their protein content by absorbency at 214 nm. The peak fractions were pooled and dialyzed overnight at 4° C. against sodium acetate buffer (pH 4.0) in the case of the BPI protein or evaporated to dryness (Speedvac, Sorval Instruments, E.I. DuPont DeMurs, Wilmington, Del.) in the case of the 15K mammalian polypeptides. It should be noted that the 15K mammalian polypeptides can be evaporated to dryness before use.

The elution profile is shown in FIG. 2 for the crude rabbit PMN extract (left panel) and the $MgCl_2$ eluate (right panel).

In FIG. 2, it can be seen that the 15K mammalian polypeptides of the present invention eluted earlier (at approximately 15 minutes) than the BPI holoprotein (at approximately 20 minutes) and there was no cross-contamination of the two eluates. In addition, the 15K mammalian polypeptides were present in about equal amounts to the BPI holoprotein (right panel, FIG. 2).

From the various stages of the isolation and purification procedure (see FIG. 1), the starting sample and products were analyzed by SDS-PAGE using the PhastGel® system (Pharmacia Fine Chemicals, Piscataway, N.J.) using a 10–15% polyacrylamide gradient gel containing 0,112M acetate, 0.112M TRIS HCl, and pH 6.4. Protein bands were visualized by Coomassie blue staining well-known in the art. The results of the SDS-PAGE analysis are shown in FIG. 3.

In FIG. 3, lane 1 is the crude PMN extract, lane 2 is the unbound proteins, lane 3 is control E. coli J5, lane 4 is E. coli J5 containing the bound proteins, lane 5 is the $Mg^{2+}$ eluate, lane 6 is the 15K mammalian polypeptides of the present invention after RPHPLC and lane 7 is BPI protein eluted from RPHPLC.

As can be seen from the data presented in FIG. 3, using the method of the present invention, both the BPI holoprotein and the 15K mammalian polypeptides (lane 6) of the present invention were (lane 7) obtained in a substantially homogeneous form after RPHPLC although two isoforms are present in a ratio of 1:3, 15KA to 15KB (see below)

BPI and the 15K mammalian polypeptides in the $Mg^{2+}$ eluate could be separated completely by HPLC. The later peak was eluted at the same acetonitrile concentration as purified rabbit BPI and was further identified as BPI by its migration upon SDS-PAGE (data not shown), and by biological and immunological assays (data not shown). The chromatogram shows in addition two earlier, closely apposed, peaks. Further separation of these two peaks was achieved by repeated RPHPLC using a shallower acetonitrile gradient of 0–70% acetonitrile over 60 minutes (as shown in Example 6 below). Both species migrated with an apparent molecular mass of 15 kDa, and are designated 15KA (earlier peak) and p15KB (later peak).

A rough estimate of the BPI and 15K mammalian polypeptides protein content in PMN extracts based on Coomassie blue staining after SDS-PAGE indicated that the two protein species were present in roughly the same amounts at about 1 mg/10 ml extract ($1.8 \times 10^9$ cell equivalents). About 400 micrograms of each protein was obtained after the purification, representing recovery of about 40%. Subsequent separation of 15KA and 15KB (described below) revealed an apparent mass ratio of approximately 1:3, respectively.

Differences between 15KA and 15KB were also observed during cation-exchange chromatography on a mono-S column. Elution of p15A required a higher NaCl concentration than that of p15B (1.3M vs. 1.1M NaCl, respectively), suggesting that the former is more basic than the latter.

EXAMPLE 2

Amino Acid Composition and $NH_2$-Terminal Sequence Analysis of the 15K Mammalian Polypeptide of the Present Invention The 15K mammalian polypeptides of the present invention were subjected to amino acid analysis. The amino acid composition (obtained from rabbit PMN) was determined using a Waters Pico-Tag amino acid analyzer (Waters Associates, Milford, Mass.) as described (Bidling-Meyer, B. A. et al., J. Chrom. 336: 93– 104, 1984). The samples were pretreated in vacuo for 24 hours at 110° C. with 5.7 N HCl containing 0.5% phenol. Isolated 15KA and 15KB were used. The results are set forth below in Table 1:

TABLE 1

| AMINO ACID | (MOL %) | |
|---|---|---|
| | 15 KA | 15 KB |
| Asx | 6.1 | 6.1 |
| Glx | 14.4 | 14.0 |
| Ser | 2.6 | 3.4 |
| Gly | 6.3 | 6.1 |
| His | 0.8 | 1.1 |
| Arg | 16.5 | 15.6 |
| Thr | 4.1 | 4.1 |
| Ala | 6.6 | 6.6 |
| Pro | 14.1 | 14.4 |
| Tyr | 1.9 | 2.2 |
| Val | 4.8 | 4.7 |
| Met | 0.2 | 0.4 |
| Cys | ND | ND |
| Ile | 4.1 | 4.1 |
| Leu | 8.3 | 8.2 |
| Phe | 5.6 | 4.7 |
| Lys | 3.2 | 3.6 |

(ND = not determined)

The values shown above represent the mole fraction (%) of each amino acid residue. "Asx" stands for asparagine and aspartic acid and "Glx" stands for glutamine and glutamic acid. The amount of cystine was not determined.

The above amino acid composition was clearly distinct from that of rabbit and human BPI (data not shown).

$NH_2$ sequence analysis of the 15K mammalian polypeptides of the present invention (obtained from rabbit PMN) was performed using the well-known Edman degradation technique (Edman, P. Eur. J. Biochem. 1: 80–91, 1967) using an amino acid sequencer (Applied Biosystems, Inc., Fullerton, Calif.). Phenylthiohydantoin derivatives of amino acids released sequentially by the Edman degradation process were analyzed by RPHPLC using an IBM 150mm C18 column (IBM Instruments, Inc., Willingford, Conn.). The results are set forth below in Table 2.

TABLE 2

| 15 KA: | Ile—Pro—His—Arg—Arg—Leu—Arg—Tyr—Glu—Glu—Val—Val—Ala—Gln—Ala—Leu—Gln—Phe—Tyr—Asn. |
|---|---|
| 15 KB: | Ile—Pro—His—Arg—Arg—Leu—Arg—Tyr—Glu—Glu—Val—Val—Ala—Gln—Ala—Leu—Gln—Phe—Tyr—Asn. |

EXAMPLE 3

The above $NH_2$-terminal amino acid sequences were also distinct from those of rabbit and human BPI as disclosed in U.S. patent application Ser. No. 228,035.

Growth Inhibition and Arrest of E. Coli J5

The 15K mammalian polypeptides obtained as set forth above in Example 1 (used as a 1:3 mixture of 15KA and 15KB respectively obtained after the first RPHPLC column) were tested for inhibition of E. coli colony formation or arrested bacterial growth in liquid medium.

Incubations were carried out for 15 minutes at 37° C. in 250 microliters sodium phosphate buffered (20 mM, pH 6.0) 0.8% nutrient broth/saline containing $10^7$ E. coli J5. The number of colony forming units was measured by plating the bacteria on nutrient agar after serial dilutions in saline. For measurement of bacterial growth, an aliquot of the incubation mixture was taken at various times, diluted 5-fold with saline and the absorbency at 550 nm was measured.

The results of the growth inhibition and growth arrest experiments are illustrated in FIGS. 4, 5 and 6.

FIG. 4 shows the results of colony formation inhibition. The results indicate that the 15K mammalian polypeptides (both 15KA and 15KB) had no antibacterial activity against *E. coli* J5 when used alone (FIG. 4, closed triangles). When added to *E. coli* together with the BPI protein, the 15K mammalian polypeptide reduced by about 3-fold the amount of BPI needed to produce growth inhibition (FIG. 4, closed circles).

Similar results were achieved in the growth arrest experiment using liquid medium (see FIG. 5). In FIG. 5, again the 15K mammalian polypeptide of the present invention had no antibacterial activity when used alone against *E. coli* J5 (FIG. 5, open squares). 0.12 micrograms of BPI caused a minimal (less than 25%) reduction in bacterial growth when used alone (closed triangles). However, the addition of the 15KA mammalian polypeptide of the present invention to 0.12 micrograms of BPI (open triangles) was almost as effective as 0.4 micrograms of BPI alone, thereby reducing by more than three-fold the amount of BPI needed to produce growth inhibition of *E. coli*.

FIG. 6 depicts the growth inhibition dose requirement for the 15K mammalian polypeptide and the BPI protein. The results in FIG. 6 indicate that the maximal potentiating effect was achieved with about 0.2 micrograms of the 15K mammalian polypeptide per $10^7$ bacteria (15 nM) using from 0.02 micrograms to 0.011 micrograms of the BPI holoprotein.

EXAMPLE 4

Potentiating Effects of the 15K Polypeptides on Bactericidal Agents

A series of experiments were conducted to determine if the 15K mammalian polypeptides (obtained as in Example 1 above) could enhance or potentiate the bactericidal effects of other killing agents, in addition to the rabbit BPI protein tested in Example 3.

The other killing agents tested included the following: (i) human BPI protein (holoprotein); (ii) the biologically active fragment of human BPI (the 25K fragment and described in co,ending, commonly assigned U.S. application Ser. No. 228,035, filed Aug. 5, 1988); (iii) polymyxin-B (an antibiotic); and (iv) normal human serum.

For both (i) the human BPI protein and (ii) the 25K fragment, the following conditions were used: incubations were carried out for 15 minutes at 37° C. in 250 microliters sodium phosphate buffered (20 mM, pH 6.0) 0.8% nutrient broth/saline containing $10^7$ *E. coli* J5. The number of colony forming units was measured by plating the mixture on nutrient agar after serial dilutions in saline. For measurement of bacterial growth, an aliquot of the incubation mixture was taken at various times, diluted 5-fold with saline and the absorbency at 550 nm was measured.

For (iii) polymyxin B, the conditions were the same as the conditions for (i) and (ii) except that the incubation was performed in minimal media containing 10% Hanks buffered salt solution and 0.2% cas-amino acids in saline, and buffered to pH 7.4 with 20 mM sodium phosphate.

For (iv) normal human serum, the conditions were the same as the conditions for (i) and (ii) above except that the pH was 7.4.

The results from the experiments in Example 3 are depicted in FIG. 7 (A through D). These results demonstrate that the 15K mammalian polypeptides of the present invention potentiated growth inhibition of *E. coli* J5 by the human BPI protein (FIG. 7A) as well as the 25K biologically active fragment of human BPI protein (FIG. 7B). No effect in terms of enhancement or potentiation of growth inhibition by polymyxin B (FIG. 7C) or normal human serum-mediated killing (7D) was observed for the 15K mammalian polypeptides of the present invention.

EXAMPLE 5

Effects on Bacterial Outer Membrane

The effects or changes produced by BPI on the bacterial outer membrane by the potentiation of BPI by the 15K mammalian polypeptides (used as a 1:3 a mixture of 15KA and 15KB) were investigated. The effects studied in two separate experiments were (1) the permeability-increasing activity; and (2) phospholipase activation.

In both experiments, incubations were carried out at 37° C. in 250 microliters of 20 mM sodium phosphate-buffered 0.8% nutrient broth/saline containing $10^7$ *E. coli* J5.

For the permeability-increasing assay, incubations were performed for 15 minutes at pH 6.0 in the presence of 50 micrograms/ml actinomycin D. Under these conditions, only bacteria rendered permeable to actinomycin D by BPI±the 15K polypeptides of the present invention and promptly lost their biosynthetic capabilities.

For phospholipase activation, the assay was performed at pH 7.4 in the presence of 0.2% bovine serum albumin (BSA) for 45 minutes. Degradation of [$^{14}$C]-oleate-labeled phospholipid of *E. coli* J5 was measured as release of radioactivity free fatty acid or lysophospholipid trapped by complexing with albumin in the supernate after centrifugation (BPI± 15K-treated bacteria).

Figure 8:
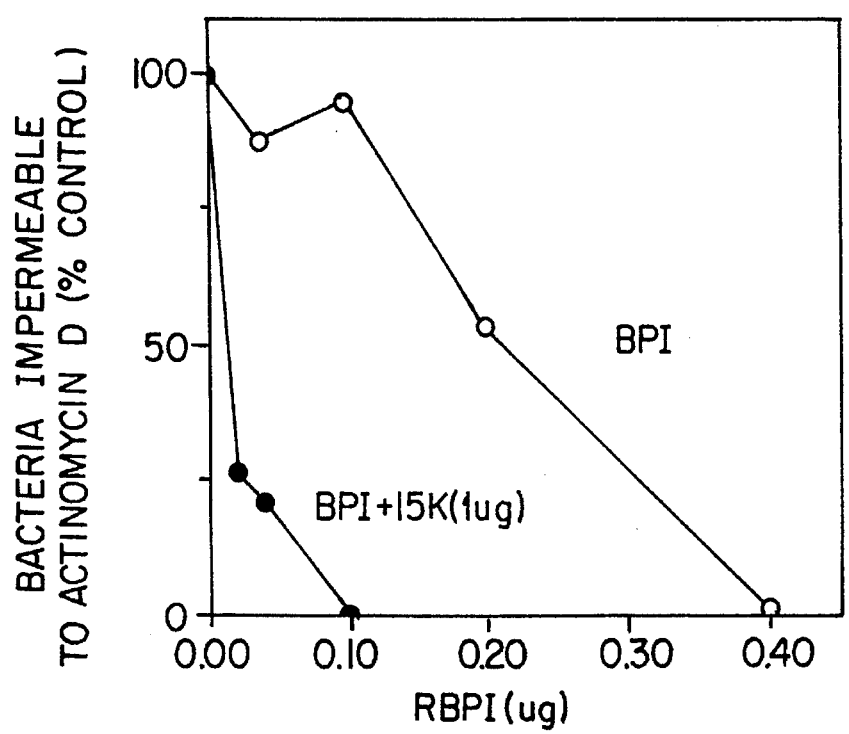
FIG. 8 is a graph comparing the permeability-increasing activity (to Actinomycin D) of the BPI protein and of the two 15K polypeptides by themselves and in combination with BPI.
Figure 9:
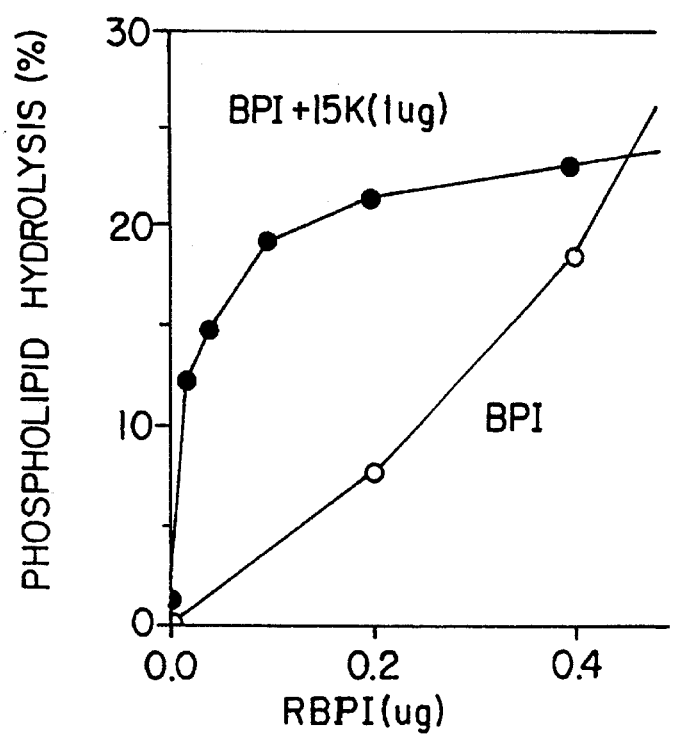
FIG. 9 is a graph comparing phospholipase activation activity in E. coli J5 of the BPI protein and the two 15K polypeptides by themselves and in combination with BPI.

The results of both experiments in Example 4 are illustrated in FIGS. 8 and 9.

The results from Example 4 demonstrate that the 15K mammalian polypeptide of the present invention also potentiated BPI effects on the permeability barrier in the outer membrane of *E. coli* (FIG. 8 closed circles) and on bacterial phospholipid degradation (FIG. 9 closed circles) when compared to bacteria treated with BPI alone (FIGS. 8 and 9, open circles).

EXAMPLE 6

Isolaton of 15KA and 15KB

The RPHPLC eluate shown in FIG. 3 was further fractionated by repeated (up to three times) RPHPLC using the techniques and equipment described in Example 2 above except using a shallower acetonitrile gradient of 0–70% acetonitrile over 60 minutes. The results are shown in FIG. 10.

Figure 10:
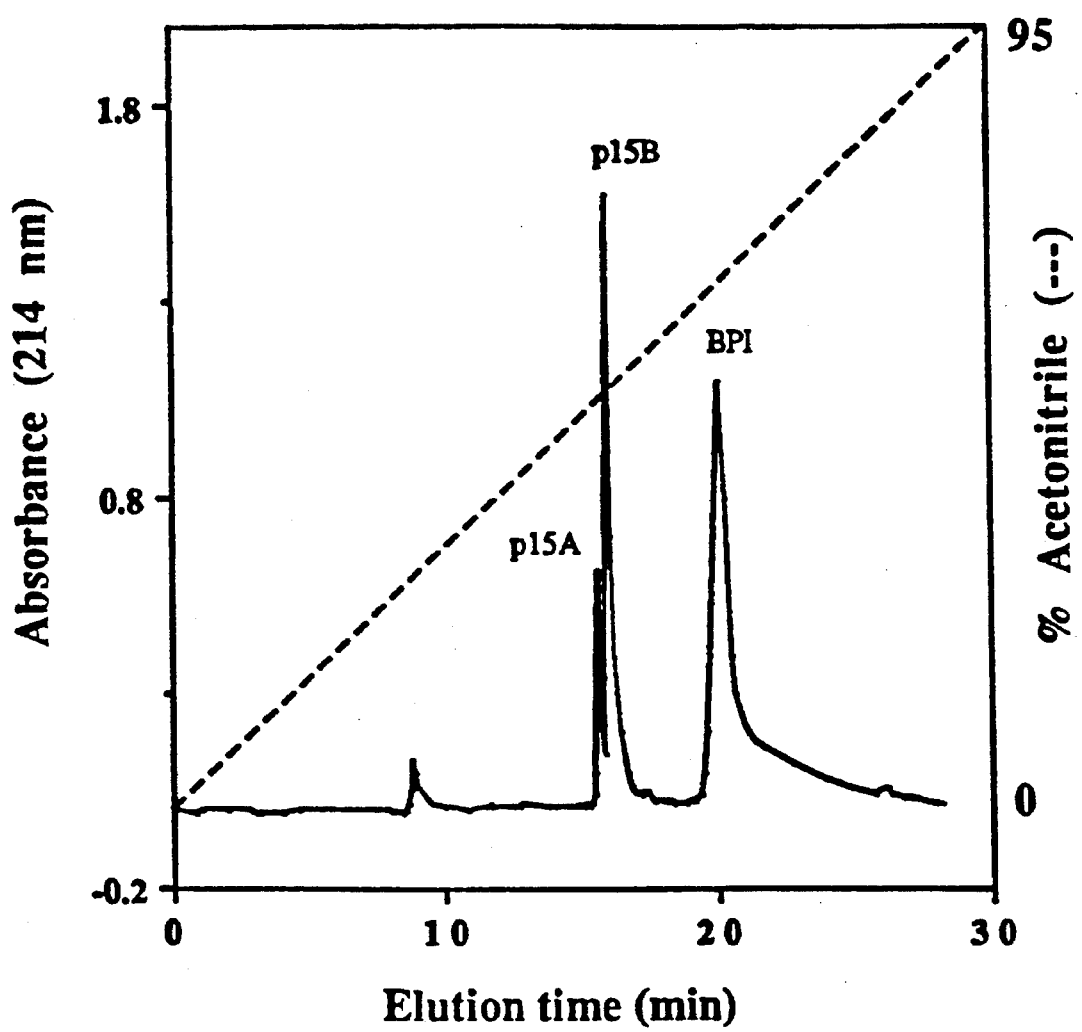
FIG. 10 is a graph showing the elution profile of BPI and each of two 15K polypeptides of the present invention from RPHPLC.

As can be seen in FIG. 10, two species were obtained after repeated RPHPLC using the condition described above. Both species had an apparent Molecular mass of 15 kDa as assayed by SDS-PAGE (data not shown).

Cation exchange chromatography was performed on an HPLC system (FPLC, Pharmacia Fine Chemicals, Piscataway, N.J.) using a Mono S column (Pharmacia). The buffer system used was 50 mM sodium acetate/acetic acid, pH 5.0 and proteins were eluted with a linear gradient of sodium chloride. Elution of protein was monitored at 214nm. The results are shown in FIG. 11.

Figure 11:
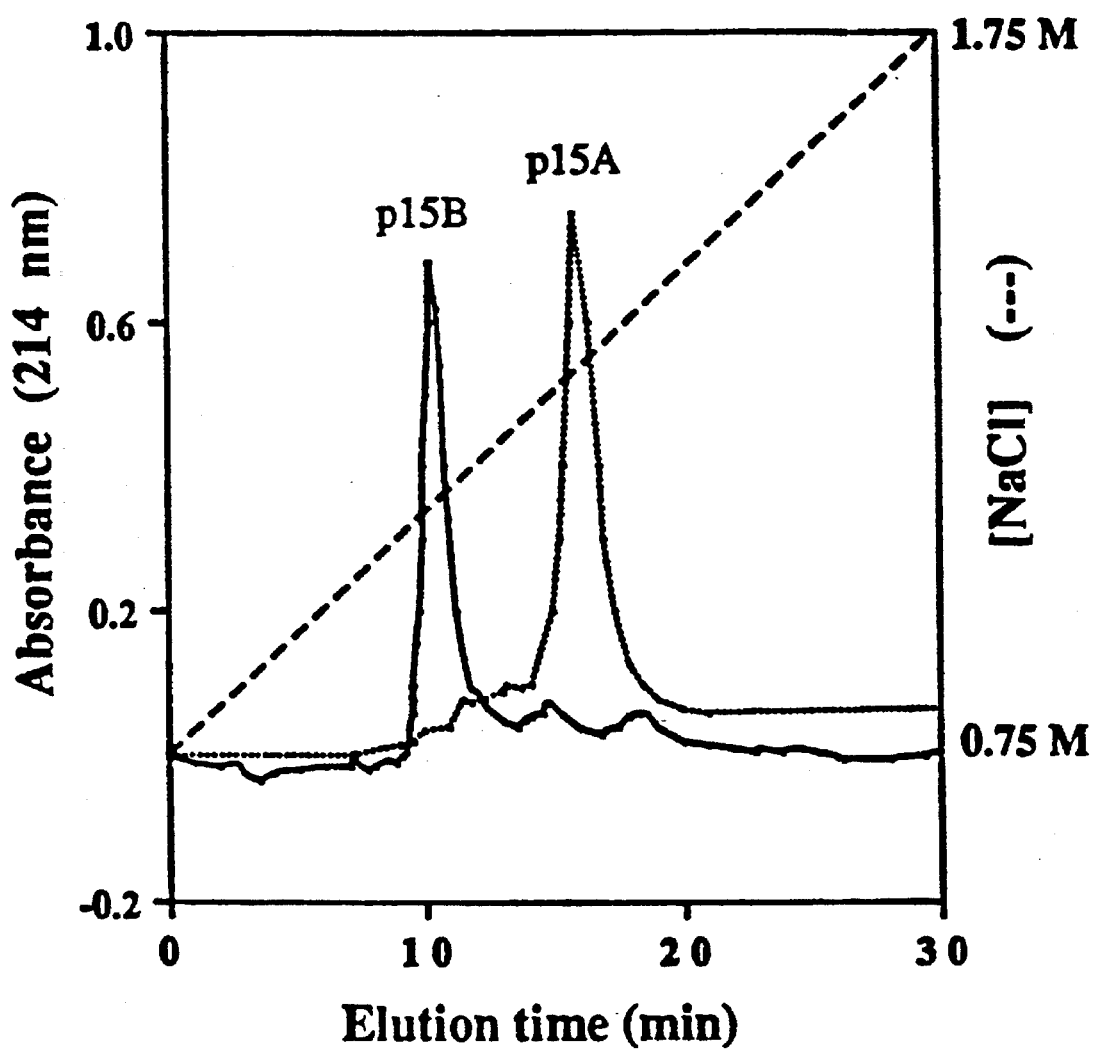
FIG. 11 is a graph showing cation-exchange chromatography of 15KA and 15KB eluting separately.

In FIG. 11, Panel (a) represents 2.5 mg crude extract; panel (b) represents 500 micrograms $Mg^{2+}$ eluate (i.e. preferentially bound proteins).

As can be seen in FIG. 11, differences between 15KA and 15KB were also observed during cation-exchange chromatography on a Mono-S column. Elution of 15KA required a higher NaCl concentration than that of 15KB (1.3M vs. 1.1M NaCl, respectively), suggesting that the former is more basic than the latter.

EXAMPLE 7

Biological Properties of the 15KA and 15KB Mammalian Polypeptides

Figure 12A:
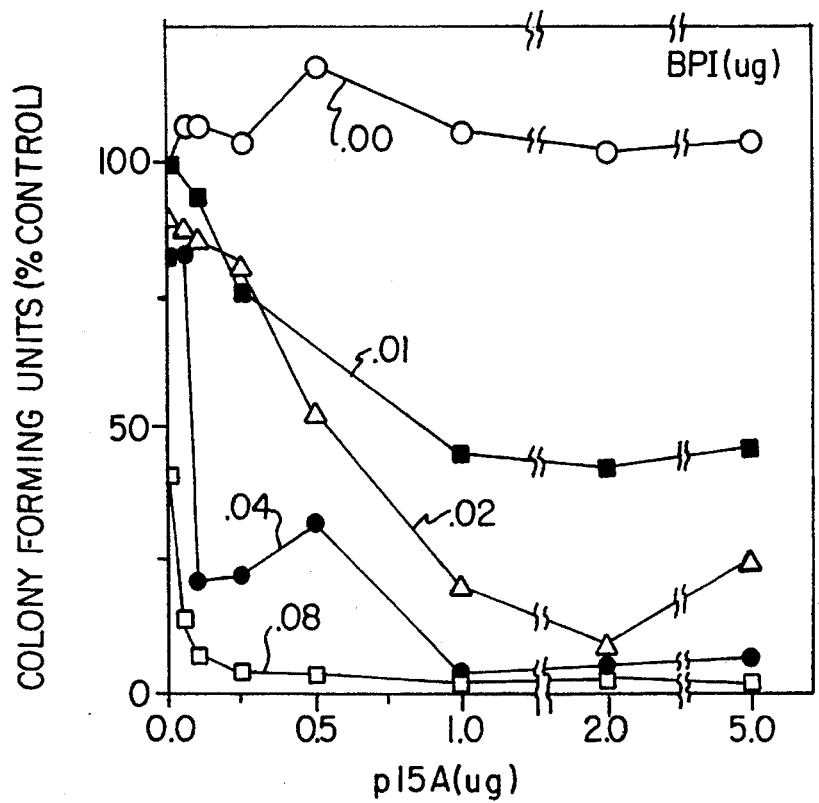
FIG. 12 is a series of graphs showing the dose-dependent effect of 15KA and/or 15KB on growth inhibition of coli J5 by BPI.

The biological effects of the isolated 15KA and 15KB were investigated. The results are shown in FIG. 12. When tested against E. coli J5, neither 15KA and/nor 15KB caused any loss of viability even when added at molar concentrations that were 100-fold higher than the minimal growth inhibitory dose of BPI (FIG. 12). However, addition of 15KA in combination with BPI markedly reduced the dose of BPI required for inhibition of bacterial growth (FIG. 12a). The magnitude of this potentiating effect was dependent on the dose of both BPI and 15KA. At a very low non-growth inhibitory BPI dose (e.g. 10ng/107 bacteria), addition of ≥1 ug of 15KA caused 50–60% growth inhibition. More complete (>95%) growth inhibition was produced at higher BPI doses, with the amount of 15KA required declining (to as little as 0.11 ug) as the BPI dose was increased (FIG. 12a). Under optimal conditions, 15KA reduced by 6–8 fold the amount of BPI needed for growth inhibition (FIG. 12).

Figure 12B:
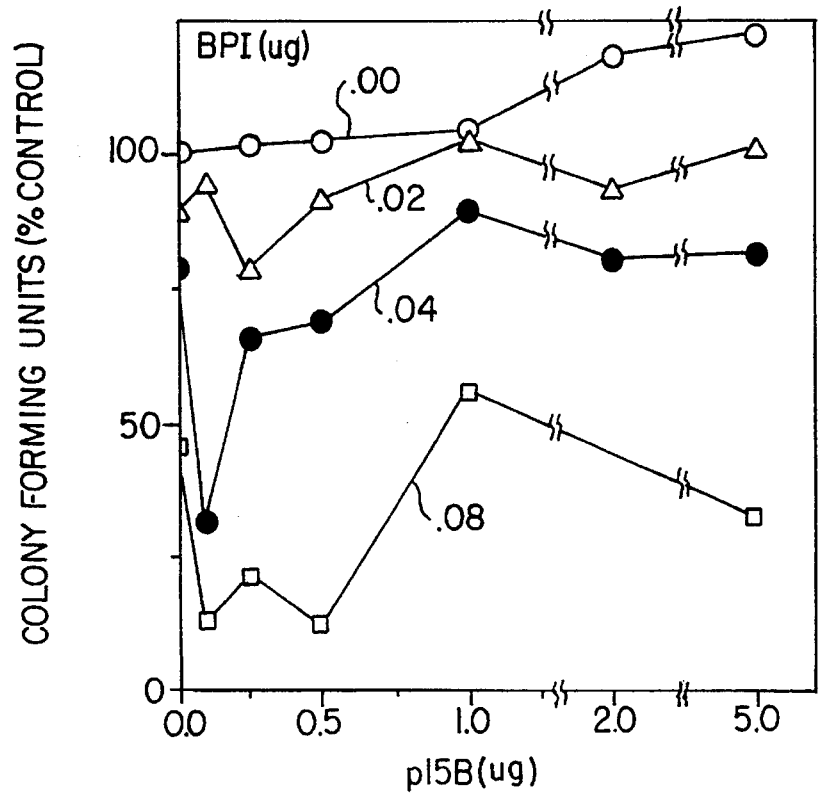

In contrast to 15KA, 15KB at low doses had a modest potentiation effect which was lost at higher doses (FIG. 12b). The absence of a potentiating effect with high 15KB doses is illustrated in FIG. 12b.

Figure 12C:
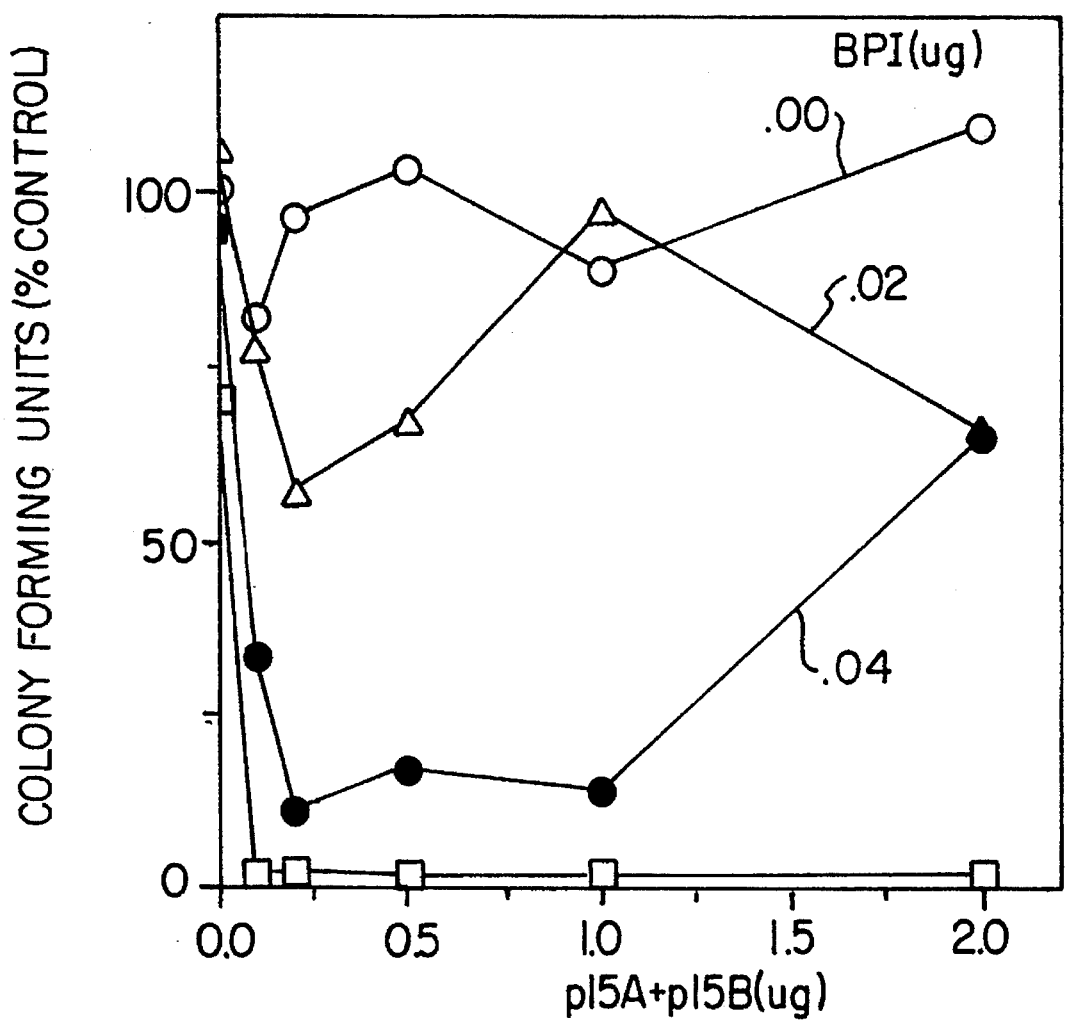

When a combination of 15KA and 15KB (15KA: 15KB 1:3) was present together with sub-inhibitory doses of BPI, significant potentiation of growth inhibition was observed at low (≤1 microgram) 15KA/15KB doses with little or no effect at higher doses (≥1 microgram),reflecting the influence of both isoforms under the former conditions, and the dominance of the 15KB effect in the latter case (FIG. 12c).

The initial growth inhibitory effect of BPI is typically accompanied by an increase in bacterial outer membrane permeability (e.g. to the normally impermeant drug actinomycin D) and activation of bacterial phospholipolysis. FIGS. 12A and 12C show that 15KA when added alone did not affect bacterial outer membrane permeability or phospholipolysis, but reduced by 10–20-fold the amount of BPI required to produce these effects. The amount of 15A required for maximal potentiation of these effects (about 2 micrograms) was similar to that required for potentiation of bacterial growth inhibition. In contrast to 15KA, 15KB caused little or no potentiation of these envelope effects of BPI (FIGS. 12b & 12c).

Figure 13A:
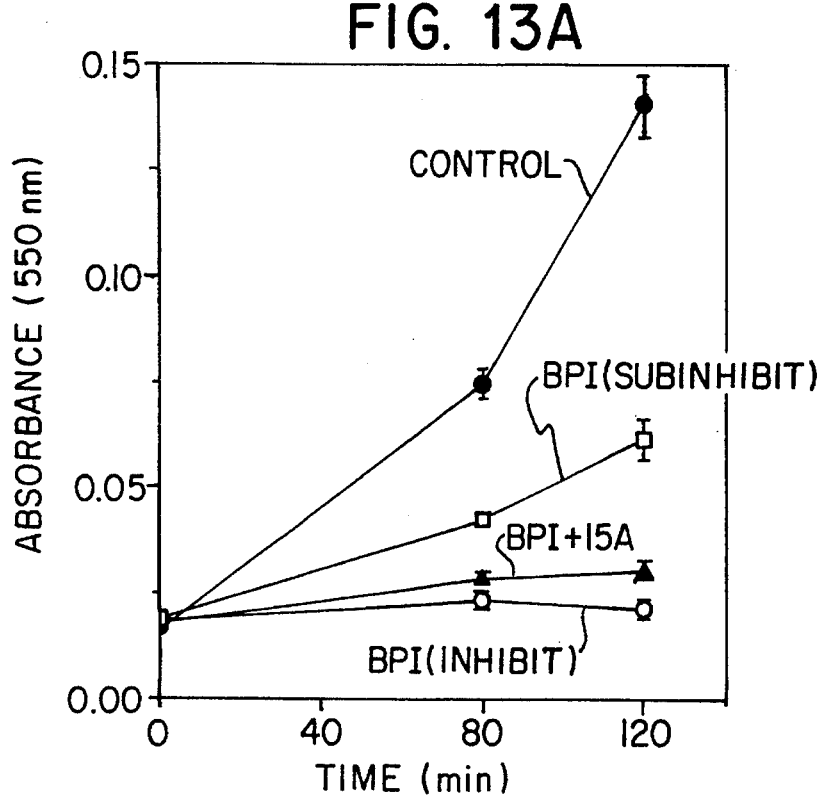
FIG. 13 (a and b) are graphs showing a comparison of effects of each of two 15K isoforms on BPI growth inhibition of E. coli J5.

The differences in the biological activites of 15KA and 15KB might reflect differences in their E. coli binding properties. However, re-exposure of the "$Mg^{2+}$+eluate" (i.e. a mixture of BPI, 15KA and 15KB) to E. coli J5 followed by elution of bound protein with 200 mM $Mg^{2+}$ resulted in recovery of the two isoforms in the same apparent mass ratio as the starting material, indicating indistinguishable binding of 15KA and 15KB under these conditions. Moreover, incubation of either 15KA or 15KB with E. coli (5 micrograms/$10^7$ bacteria) in the absence or presence of BPI (30 ng) resulted in absorption of similar amounts of both isoforms in all cases (FIG. 13). Thus, neither 15KA nor 15KB requires BPI for binding to E. coli and the differences in their biological properties are not correlated with recognizable differences in binding.

Figure 13B:
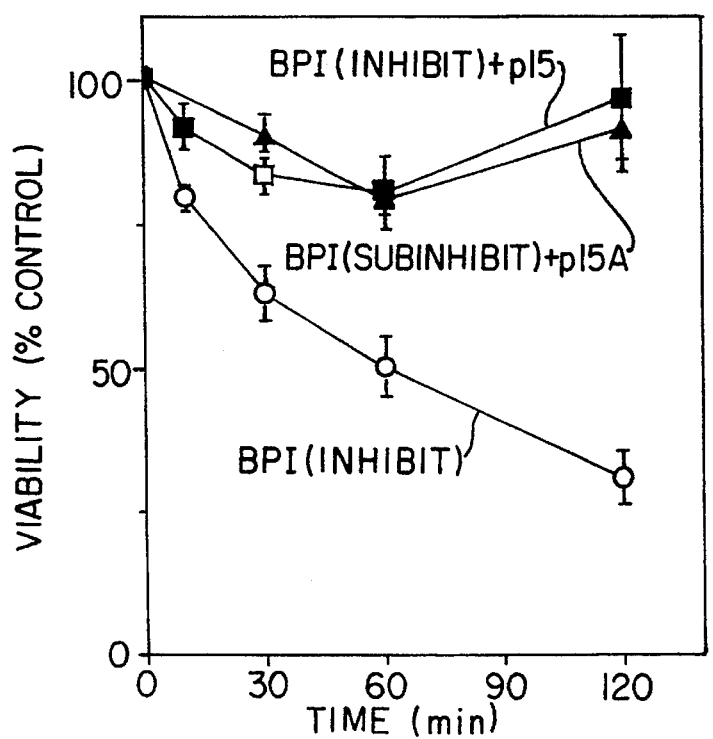

In contrast to 15KA, 15KB at low doses had a modest potentiation effect which was lost at higher doses (FIG. 13b). The absence of a potentiating effect at high 15KB doses is illustrated in FIG. 13b.

When a combination of 15KA and 15KB (15KA:15KB 1:3) was present together with sub-inhibitory doses of BPI, significant potentiation of growth inhibition was observed at low (≤1 microgram) 15KA 15KB doses with little or no effect at higher doses (≥1 microgram), reflecting the influence of both isoforms under the former conditions, and the dominance of the 15KB effect in the latter case (FIG. 13c).

The potentiating effect of the 15K mammalian polypeptides proteins on BPI growth inhibition was also seen with the more BPI-resistant smooth E. coli 0111:B4 (results not shown).

EXAMPLE 8

Cloning of the 15K Mammalian Polypeptides of the Present Invention and Determination of their Amino Acid Sequence In the Example present below, the following materials and methods were used.

Purification of p15's

The 15 kDa protein isoforms were purified from rabbit PMN and their identity monitored by SDS-PAGE, reverse-phase HPLC, and BPI modulating assays as described above.

Amino Acid Sequencing

The amino terminal amino acid residues of chromatographically separated p15's were analyzed by automated sequential Edman degradation on a protein peptide microsequencer (Porton Model 2090E).

Isolation of cDNAs

A bacteriophage Lambda gt10 cDNA library prepared from the bone marrow of a New Zealand White rabbit was kindly provided by Dr. Tomas Ganz (Will Rogers Pulmonary Research Laboratory, UCLA) and Steve Leong (Dept. Developmental Biology, Genentech). The library was initially screened by standard methods (Sambrook, J. et al., *Molecular Cloning, A Laboratory Manual*, p. 8.46–8.52, Cold Spring Harbor Press, N.Y., 1989) with a synthetic 81 base pair (bp) oligonucleotide probe constructed on the basis of N-terminal sequences and end-labelled with $^{32}$p ATP using polynucleotide kinase (Gibco-BRL, Grand Island, N.Y.). The sequence was: 5' ATT CCT CAC AGG AGG CTG AGG TAT GAG GAG GTG GTG GCT CAG GCT CTG CAG TTC TAC AAT GAA GGC CAG CCT GGC AAT CCC 3'. A second screen of the library was performed using the N-terminal AspHi p15R cDNA fragment labelled by the random hexamer method (Pharmacia, Piscataway, N.J.).

Sequencing cDNA's from positively hybridizing plaques were sequenced either directly in the Lambda vector by the thermal cycle sequencing method as described by the manufacturer (Gibco-BRL) or after subcloning into M13mp18 by the dideoxy-chain termination method (Sanger F. et al., *Proc. Acad. Sci. USA* 74: 5463–67, 1977). For all sequences shown, both strands were sequenced at least twice.

Sequence Analysis

DNA and deduced protein sequences were analyzed using the GCG Sequence Analysis Software Package (Deverewy, J. et al., *Nuc. Acid. Res.* 12: 387–395, 1984). Protein homologies were identified using the FASTA and TFASTA programs (Pearson, W. R. et al., *Proc. Natl. Acad. Sci. USA* 85: 2445–48, 1988) on the GenBank, Swiss-prot, and National Biomedical Research Foundation data bases. Sequences were aligned based on a pair-wise comparison using GAP and were manually positioned using the LINEUP and PRETTY programs. The program PRETTYBOX (courtesy of Mr. Richard Westerman, AIDS Center Laboratory for Computational Biochemistry, Purdue University) was used to obtain output for multiple sequence alignments.

Anti-p15 Serum & Radioimmunoassay p15 antiserum was generated in Guinea pigs by repeated challenge with a 1:1 mixture of the p15A and p15H/R species. Pre-immune sera were collected from the same guinea pigs before immunization. Radioimmunoassay (RIA) of p15's with anti-p15 sera was carried out as previously described (Weiss, J. and Olsson, I., *Blood* 69: 652–659, 1987). Bound antibody was detected with $^{125}$I-protein G (New England Nuclear, Boston, Mass.) and measured in a Gamma Counter (Beckman Model 5500). The antiserum recognized both p15 species in a dose-dependent manner whereas pre-immune serum was unreactive. The antiserum was found to be entirely cross-reacting with respect to the two major species as judged by the fact that its depletion by incubation with one of the chromatographically separated species immobilized on nitrocellulose depleted >95% of reactivity towards the other and vice versa. Depletion of the antisera with p15's depleted >90% of reactivity toward rabbit PMN detergent extracts.

Release of p15's from Degranulating PMN

Rabbit PMN were collected from glycogen-elicited sterile peritoneal exudates of New Zealand white rabbits (Elsbach, P. and Schwartz, I. L., *J. Gen. Physiol.* 42: 883–898, 1959) and cells were resuspended at a concentration of $2\times10^7$/ml. To induce degranulation, PMN were treated with cytochalasin B (5 µg/ml) for 30 minutes at 37° C., followed by addition of formyl— Met—Leu—Phe (fMLP, $10^{-6}$M) and an additional 30 minute incubation. Soluble proteins that were released extracellularly were separated from those that were cell-associated by centrifugation (3,000×g, 5 minutes). The cell pellet was solubilized by sonication in 1% triton-X-100 and aliquots from both supernatant and pellet were assayed spectrophotometrically for marker enzymes as described (Wacker, W. E. C. et al., *N. Engl. J. Med.* 255: 449– 456, 1956; Talalay, P. et al., *J. Biol. Chem.* 166: 757–772, 1946; Smolelis, A. and Hartsell, S. E., *J. Bact.* 58: 731–736, 1949). LDH by the increase in absorbance (340 nm) accompanying the conversion of NAD+to NADH (Statzyme, Worthington); β-glucuronidase by the increase in absorbance (550 nm) accompanying the release of phenolphthalein from its β-glucuronate (Boehringer Mannheim), and lysozyme by the decrease in absorbance (450 nm) accompanying hydrolysis of a *Micrococcus lysodeikticus* cell wall preparation (Sigma, St. Louis, Mo.). Aliquots of pellet and supernatant were treated with 1% triton-X-100\1% deoxycholate prior to p15 RIA. Percent release of each protein was calculated as the difference in activity of supernatants from FMLP-treated and untreated cells divided by the total activity (pellet + supernatant) recovered from PMN treated with cytochalasin B alone.

RESULTS

Heterogeneity of p15 Primary Structures

N-terminal amino acid sequence analysis of the two p15 isoforms mentioned above (p15A and p15B) showed that 19 of the first 20 residues were identical but the identity of the third residue was ambiguous. Repeated N-terminal sequence analysis of these two purified p15 preparations has now established that alanine is the third residue in the isoform that strongly potentiates the early effects of BPI ("p15A"), whereas both histidine ("p15H") and a small amount of arginine ("p15R") were detected in the third cycle of Edman degradation of the less active isoform(s) (p15B) as shown in Table 2 below. These findings suggested that there are at least 3 members of this p15 protein family with closely similar but distinct primary structures.

TABLE 2

| | N-terminal Amino Acid Sequences of p15's | | | | | | | | | | |
|---|---|---|---|---|---|---|---|---|---|---|---|
| | | | | Amino Acid # | | | | | | | |
| Isoform | 1 | 2 | 3 | 4 | 5 | 6 | 7 | 8 | 9 | 10 ... | 20 |
| p15H/R | I | P | H/R | R | R | L | R | Y | E | E | N |
| p15A | I | P | A | R | R | L | R | Y | E | E | N |

Amino acids in Table 2 above are represented by the single letter code. p15A indicates the isoform containing an alanine at position three; p15H/R indicates a chromatographically homogeneous species that has two components: a major one having histidine at position 3 and a minor one having arginine, all other N-terminal amino acids are identical.

Cloning of p15H and p15R cDNA's

To more fully define the primary structures of the p15's the cloning of their cDNA's was pursued. A rabbit bone narrow cDNA library was screened first with a synthetic oligonucleotide probe, constructed on the basis of the N-terminal amino acid sequence of purified 15 kDa proteins and then with a p15 cDNA fragment. Two groups of closely similar clones were identified, each containing an open reading frame (ORF) encoding p15(s) as judged by the identity of the deduced amino acid sequences with the determined N-terminal amino acid sequences of purified p15's as shown in FIG. 14.

In FIG. 14, the underlined amino acids are identical to those of p15H and p15R, respectively as determined by amino acid sequencing. The p15R cDNA sequence is shown numbered I to 798 with a p15H cDNA sequence above it numbered 1'to 798'. Dots indicate nucleotide identity. The two divergent nucleotides in the coding region of p15H and the amino acids encoded are shadowed above and below the p15R sequence, respectively. The most complete p15H clone extended from base pair (bp) 15 to the polyA tail and was sequenced in the positive strand to bp 428 (p15R numbering) and in the negative strand from bp 67 to 98 to verify the codon representing the third amino acid of the mature protein. The G nucleotides at base pairs 3, 6, and 12 indicate that the initiator ATG is in a favorable Kozak translational consensus sequence (Kozak, M. *J. Biol. Chem.* 108:229–241, 1989). The star indicates the stop translation codon and the polyadenylation signal (AATAA) is found at bp 764.

Each ORF encodes a mature protein of 117 amino acids (calculated molecular weight 13.7 kDa) preceded by a hydrophobic stretch of 20 residues apparently representing a signal sequence. The encoded proteins are rich in arginine and proline, contain 4 cysteines, and lack a potential N-linked glycosylation site. The two groups of clones differed only at two nucleotide positions, one encoding His-3 and Arg-88, the other Arg-3 and Trp-88. These findings confirm that p15H and p15R are very closely similar but distinct isoforms.

Structural Homologies

A computerized homology search revealed that the p15s are structurally related to 2 other leukocyte proteins as shown in FIG. 15: (1) cathelin (34% identity), a 11.7 kDa protein from porcine leukocytes with potent cysteine protease inhibitory activity toward papain and cathepsin L (Ritonja, A. et al., *FEBS Letters* 255: 211–214, 1989; Kopitar, M. et al., *Biochem. Biophys. Hopp. Sey.* 370: 1145–1151, 1989) and (2) CAP-18 (30% identity) a 18 kDa protein, reported to exhibit lipopolysaccharide (LPS) binding and neutralizing activity (Larrick, J. W. et al., *Biochem. Biophys. Res. Comm.* 179: 17–175, 1991).

In FIG. 15, amino acids are represented by the single letter code. Residues identical between family members are boxed in black while similar ones are shaded grey. The four aligned cysteines are indicated by arrows. The p15's possess 34% amino acid identity over 96 residues to cathelin and 30% identity over 107 amino acids to CAP-18. The Z at cathelin's N-terminus indicates that it is blocked with pyrrolidonecarboxylic acid.

Moreover, comparison of cathelin and CAP-18 revealed the previously unreported fact that the two proteins are closely related (65% amino acid identity). Cathelin, CAP-18 and p15's -H and -R each contain four cysteine residues that are aligned exactly between the p15's and CAP-18, and, with the introduction of a four amino acid gap between the second and third cysteines, also with cathelin. Alignment of the proteins begins near their mature N-termini. Size differences correspond to variable C-terminal lengths: cathelin is 43 residues shorter than CAP-18 at this end and the p15's align with a 25 amino acid internal gap near CAP-18's C-terminus.

The proteins differ in their amino acid composition and charge properties. The p15s are richest in arginine, CAP-18 in lysine and leucine and cathelin in proline and leucine. Both p15s and CAP-18 are strongly cationic with calculated isoelectric points (pIs) of 11.7 and 10.1 respectively, whereas cathelin is acidic having a pI calculated and measured at 4.8 and a net charge of −2 (Ritonja, A. et al., supra; Kopitar, W. et al., supra). The p15s contain an arginine-rich region near the C-terminus (residues 85–102, containing 9 of a total of 21 arginines) while the C-terminal region of CAP-18 (residues 109– 142) has a very high concentration of both lysines (9) and arginines (5).

Evidence for Granule-Association

For a preliminary assessment of the intracellular localization of the p15's, freshly isolated peritoneal exudate PMN were treated with fMLP and cytochalasin B to stimulate degranulation.

The results are set forth in Table 3 below.

TABLE 3

| Release of Proteins from DeGranulating PMN | | |
|---|---|---|
| Protein | Localization | % Release |
| LDH | Cytosol | 2 ± 0.3 |
| β-glucuronidase | Primary Granules | 23 ± 4 |
| Lysozyme | Primary & Secondary Granules | 31 ± 1 |
| p15's | (Granules?) | 24 ± 8 |

In Table 3 above, the percent release of lactate dehydrogenase (LDH), β-glucuronidase, lysozyme, and p15's were measured and calculated as described above. The data represent the mean ±the standard error of the mean of four independent determinations.

Table 3 shows that extracellular release of p15's is comparable to that of β-glucuronidase and lysozyme, respectively, primary granule and both primary and secondary granule-associated proteins. This result and the presence of typical signal sequences in their cDNA's suggest that the p15's are also granule-associated proteins.

DISCUSSION

The discovery of homology of p15s to CAP-18 and cathelin identifies a novel family of low molecular weight leukocyte proteins. That the overall structure of these proteins is similar is further supported by the shared positioning of their four cysteines. Both the p15s and CAP-18 are highly cationic, consistent with the strong attraction of the p15s for the negatively-charged lipopolysaccharide-containing outer envelope of *E. coli* (Ooi, C. E. et al., *J. Biol. Chem.* 265: 15956– 962, 1990) and the purported binding of CAP-18 to isolated LPS (Larrick, J. W. et al., Supra). Homology between p15's and CAP 18, then, may relate to shared LPS binding properties. In contrast, the charge properties of catbelin are very different, a surprising finding because of the very high degree of identity (65%) between the pig-derived cathelin and the rabbit CAP-18. It should be noted, however that the differences in net charge are entirely attributable to the C-terminal end of CAP-18 that is absent in cathelin. Moreover, only the C-terminal fragment of CAP-18 has been isolated and it is this portion of the molecule that is said to manifest LPS-binding and neutralizing activities (Young, N. S. et al., *J. Clin. Invest.* 51: 1790–1797, 1972). The N-terminus of this C-terminal fragment is only 4 residues removed from the C-terminus of catbelin. Given the high degree of homology between these proteins from two different animal species it is speculated that cathelin is in fact the N-terminal fragment of a pig homology of CAP-18. If this is so it would raise the possibility that proteins belonging to this family of structural homologs may be bi-functional containing both a cysteine protease inhibitory domain and a highly cationic C-terminal LPS-binding domain.

Among the biologic effects of LPS is the activation of proteases in the body fluids, resulting in triggering of a complex network of proteolytic cascades that are part of the host responses to endotoxin (Young, N. S. et al., supra;

Colman, R. W., *New Engl. J. Med.* 320: 1207–1209, 1989). In addition, specific cysteine proteases are required for maturation of cytokines (e.g. interleukin-1β) that are induced by LPS (Thronberry, N. A. et al., *Nature* 356: 768–774, 1992). Important regulatory roles for proteins that can both recognize LPS and modulate the proteolytic events it initiates are envisioned.

The ability of these proteins to fulfill such functions must depend on their location. The presence of a typical signal sequence (FIG. 15) encoded by the p15 cDNAs and the demonstration that the release of p15s from stimulated PMN is comparable to that of known granule proteins (Table 3) are consistent with a granule localization of the p15s and with their appearance extracellularly under conditions that cause degranulation. The CAP-18 cDNA also encodes a signal sequence (Larrick, J. W. in press in *Inflammation*, eds. Gallin, J., Goldstein, I. M. & Snyderman, R., Second Edition, Raven Press, N.Y.) and preliminary results have indicated that cathelin may also be granule-associated.

The structural characterization of the p15s has led to the recognition of a novel family of leukocyte proteins that may share more than one function.

EXAMPLE 9

LPS-Induced Release of Tumor Necrosis Factor (TNF) in Whole Blood

The p15's of the present invention will be tested for their ability to inhibit TNF release, with and without BPI, in whole human blood ex vivo. This assay is recognized by those of ordinary skill in the art as being predictive of in vivo efficacy.

LPS-triggered release of TNF in whole blood ex vivo will be carried out as described by Desch et al. (*Lymphokine Res.* 8:141, 1989) except that blood will be collected into tubes containing citrate as an anti-coagulant (Becton-Dickinson, Lincoln Park, N.J.). Detection of TNF by ELISA will be carried out using a commercially available test kit (Biokine TNF Test Kit, T Cell Sciences, Cambridge, Mass.).

To determine if the potent endotoxin-neutralizing effects of BPI (and fragments) is potentiated by the 15KDa proteins of the present invention, the effect of the proteins, in the presence or absence of BPI, on the production of TNF in whole blood after incubation with LPS (Desch et al., supra) will be examined. Addition of LPS to whole blood triggers a dosedependent synthesis and extracellular release of TNF (Desch et al., supra).

Addition of human BPI to whole human blood before adding LPS (such as $R_e$ 595) causes a dose-dependent inhibition of TNF accumulation, over at least 30-fold range of LPS doses (0.1–3 ng/ml). The 15KDa proteins (together and separately) of the present invention will be assayed at concentration of between 0.1 and 3 ng/ml with and without BPI at the same concentrations (0.1–3 ng/ml). It is expected that the 15KDa proteins of the present invention will potentiate the inhibition of LPSoinduced TNF release caused by BPI. That is to say, the 15KDa proteins of the present invention will increase the inhibition of TNF release caused by BPI, especially at lower (non-optimal) BPI concentrations.

EXAMPLE 10

In the present Example, the following materials and methods were employed:

Tryptophanyl Cleavage Analysis of Purified Proteins. N-chlorosuccinimide/urea (NCS/urea) was used for the selective cleavage of tryptophanyl peptide bonds (Schechter, Y. et al. *Biochem* 15:5071–5075, 1976; Lische, M. A. et al., *J. Biol. Chem.* 252:4976–4980, 1977) according to Lische and Ochs (Lischwe, M. A. et al. *Anal. Biochem.* 127:453–457, 1982) with slight modifications. After SDS-PAGE of 15 kD isoforms (1 μg), gels were stained with 0.05% Coomassie brilliant blue (Bio-Rad, Richmond, Calif.) in 40% methanol/10% acetic acid for 20 min at 37° C.. After destaining protein bands were cut out and stored at −20° C. until use. Gel slices were first washed with distilled water for 20 min with one change and then incubated with urea buffer containing 1 g urea/1 ml distilled water/1 ml 17.4M acetic acid for 20 min with one change. Slices were then incubated for 10 min at 37° C. in urea buffer with or without 0.015M NCS (Sigma, St. Louis, Mo.). NCS/urea was removed by washing four times with distilled water: twice briefly and twice for ten minutes. Finally, slices were equilibrated in 10% glycerol, 100 mM DTT, 0.001% bromphenol blue, 3% SDS, and 0.0625M Tris-HCl, pH 6.8 for 40 min with one change. Cleavage products were resolved on 1 mm 14% polyacrylamide gels.

Binding of Proteins to LPS-Coated Beads. Magnetic beads ($4 \times 10^7$ tosylactivated Dynabeads M-450, Dynal A. S., Oslo, Norway) were prepared by incubating for 48 h at room temperature (RT) on a rotator with 0.1M sodium carbonate buffer (pH 9.5) with or without 1 mg/ml ReLPS (US Biochemical Corp.) dispersed by sonication (Sonic Dismembrator, Fisher Scientific, Springfield, N.J.) at 30% maximum output for 2 min. Thereafter, the beads were collected with a magnetic particle concentrator (Dynal), washed four times with Hank's Balanced Salt Solution (HBSS, GIBCO Laboratories, Grand Island, N.Y.) and stored at 4° C. in HBSS containing 0.1% sodium azide. Binding of the p15s (2 μg) to these beads was assessed after preincubation (37° C., 30 min, rotating) with 0, 1, 10, or 100 μg/ml ReLPS in 200 μl HBSS. Preincubated samples were then incubated with $5 \times 10^6$ LPS-coated beads or control beads for 30 min at 37° C. on a rotator, after which beads were washed four times with HBSS containing 0.05% Tween 20. Proteins were eluted from the beads by heating for 2 min in 20 μl SDS sample buffer (2% SDS, 2,5% DTT, 20% glycerol, 0.001% bromphenol blue, in 0.05M Tris-HCl pH 6.9) and resolved by SDSPAGE on 14%, 1 mm polyacrylamide gels.

Northern Blot Analysis. Total RNA was isolated from flash frozen tissues of a sacrificed New Zealand white rabbit using RNAzol B reagent according to the manufacturer's directions (Biotecx Laboratories, Tex.). Briefly, tissue samples were homogenized in RNAzol B with a few strokes in a Potter-Elvejhem glass-Teflon homogenizer, the homogenate extracted with chloroform, and the RNA in the aqueous phase precipitated with isopropanol. RNA was quantitated by measuring absorbance at 260 nm and its integrity verified by agarose gel electrophoresis. mRNA was isolated from total RNA by oligo(dT)-cellulose chromatography using the QuickPrep Micro mRNA Purification Kit (Pharmacia) according to the manufacturer's instructions. For Northern blotting, RNA from each tissue was electrophoresed on 1.2% agarose/formaldehyde gels and blotted onto nitrocellulose paper (Schleicher & Schuell) by capillary transfer (Ausbel, F. M. et al. *Current Protocols in Molecular Biology*, John Wiley and Sons, pp. 4.9.1–4.9.7, 1989). Blots were probed with the BamHI fragment of the p15 (R-3,W-

88) cDNA or a 2 kb fragment of the human actin cDNA (Grundig, P. et al. *Mol. Cell. Biol.* 3:787–1795, 1983; the actin cDNA insert of clone pHFβA-1 was the kind gift of Michael Jeffers Department of Pathology, NYU School of Medicine) labelled with $^{32}$P-dCTP by the random hexamer primer method.

Anti-p15 serum & Radioimmunoassay. Antiserum was generated in Guinea pigs by repeated challenge with a 1:1 mix of the p15A and p15B species (Ooi, C. E. et al., *J. Biol. Chem.* 265:15956–15962, 1990) purified from pooled rabbit PMN. Preimmune sera were collected from the same guinea pigs before immunization. Western blotting of rabbit PMN lysates to verify antisera specificity (results not shown) as well as radioimmunoassay (RIA) of p15's were performed as previously described (Ooi, C. E. et al. Supra). In the RIA, bound antibody was detected with $^{125}$I-protein G (NEN, Boston, Mass.) and measured in a Beckman Gamma 5500 Counter. The antiserum recognized both p15 species in a dose-dependent manner whereas preimmune serum was unreactive. The antiserum cross-reacted with the two major species as judged by the fact that its depletion by incubation with one of the chromatographically separated species immobilized on nitrocellulose depleted >95% of reactivity towards the other and vice versa. Depletion of the antisera with p15's removed > 90% of reactivity toward rabbit PMN detergent extracts.

Immunofluorescence. Fluorescent staining for p15s was performed as previously described. Rabbit cells were collected by sedimentation at 100×g for 10 min from heparinized blood and from sterile inflammatory exudates 18–21 hours after intraperitoneal injection of 300ml of physiological saline containing glycogen (2.5 mg/ml). Blood cells were treated with distilled water for 30 sec before reconstitution of isotonicity to reduce the ratio of erythrocytes to white blood cells. Cells were resuspended in phosphate buffered saline (PBS; 0.8% (w/v) NaCl, 0.02% KCl, 0.12% $Na_2HPO_4$, 0.02% $KH_2PO_4$, pH 7.4) to 5× $10^5$/ml. Cell smears were prepared by spinning (5 min, 500 rpm) onto microscope slides using a cytocentrifuge (Cytospin 2, Shandon). Cells were fixed with formalin/acetone buffer (9.3% (v/v) formalin, 45% acetone, 1 mM $Na_2HPO_4$, 6mM $KH_2PO_4$), rinsed and soaked in PBS, blocked with PBSA (0.2% bovine serum albumin in PBS) and 10% heat treated normal rabbit serum, and stained by sequential exposure to anti-p15 serum or pre-immune serum (0.05% in PBSA) and 2% rhodamine-conjugated goat anti-guinea pig IgG (Kirkegaard & Perry Laboratories) in PBSA. Slides were mounted with PBS/glycerol (1:9 v/v) and viewed with a Nikon Labophot microscope with a microflex UFX-II photomicrographic attachment.

RESULTS

Figure 16:
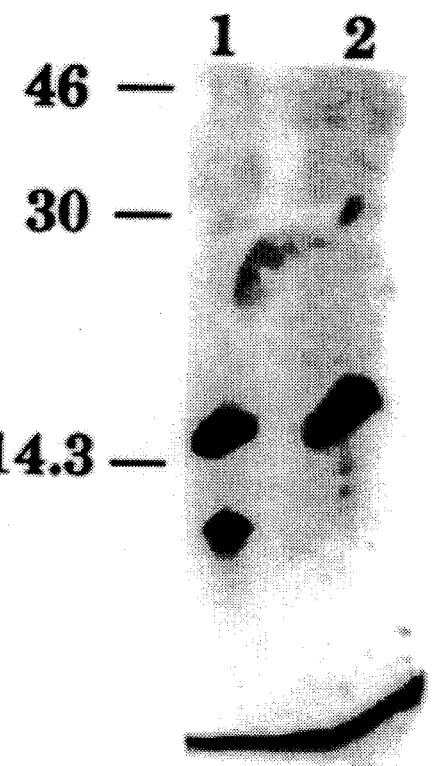
FIG. 16 is an SDS polyacrylamide gel showing the cleavage of the p15A isoform by N-chlorosuccinimide/urea.

Structural Comparison of p15s Purified from a Single Rabbit. Since the bone marrow cDNA library described above in the previous Examples was prepared from a single rabbit, the presence of distinct p15 cDNAs implied that a single rabbit can express multiple p15 isoforms. This was confirmed at the protein level by purification of p15s from the peritoneal exudate PMN of a single rabbit. Two distinct isoforms were recovered that corresponded both chromatographically and functionally (results not shown) to the more and less active p15 species (isoforms A and B, respectively, as originally purified from pooled PMN of multiple rabbits; Ooi, C. E. et al. Supra). Automated N-terminal amino acid sequencing revealed that both isoforms contained a histidine residue at position three. However, only the "A" form of p15 was cleaved by treatment with NCS/urea (FIG. 16) generating a major fragment of approximately 10 kD consistent with the presence of a tryptophan residue at position 88 and hence showing similarity in this respect to one of the cloned forms. In contrast, the "B" form was not cleaved and may thus represent the product encoded by the p15 (H-3, R-88) cDNA.

Figure 17A:
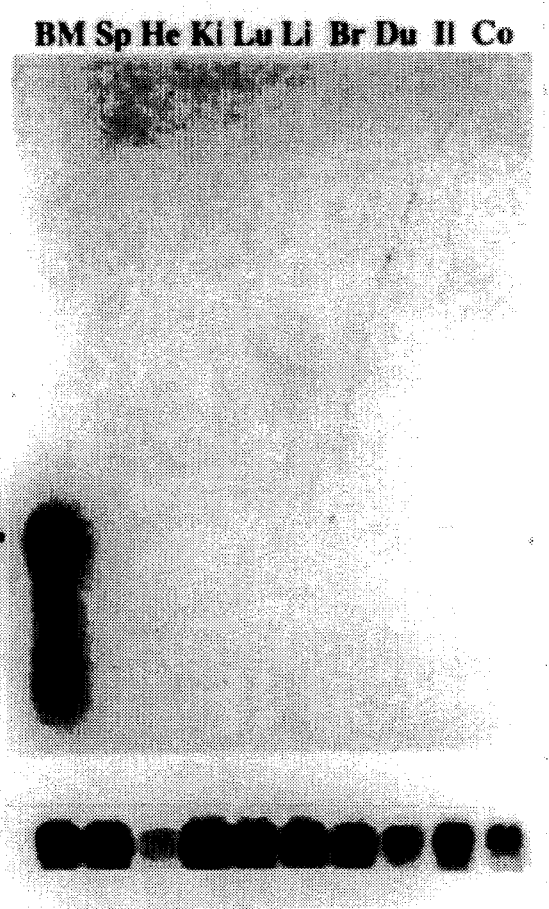
FIG. 17 is a Northern Blot containing total RNA isolated from bone marrow (BM), brain (Br), lung (Lu), heart (He), liver (Li), kidney (Ki), duodenum (Du), ileum (I1), and colon (Co) probed with the BamHl fragment of the p15 (Arg-3, Trp-88) cDNA (A) or with an actin cDNA fragment (B) as a control.

Cellular & Subcellular Localization. To assess the tissue distribution of p15 mRNA, a Northern blot containing total RNA from a number of organs of a New Zealand white rabbit was probed with a fragment of the p15 (R-3, W-88) cDNA. Transcript(s) of 950 nt was detected in bone marrow but in none of the other tissues tested: brain, lung, heart, liver, kidney, spleen, duodenum, ileum, and colon (FIG. 17). The signal was enhanced by enriching bone marrow RNA for polyA$^+$RNA (i.e. mRNA) confirming that hybridizing RNA corresponded to mRNA (results not shown). Thus, genes encoding p15s appear to be selectively expressed by cells of bone marrow origin.

Figure 18A:
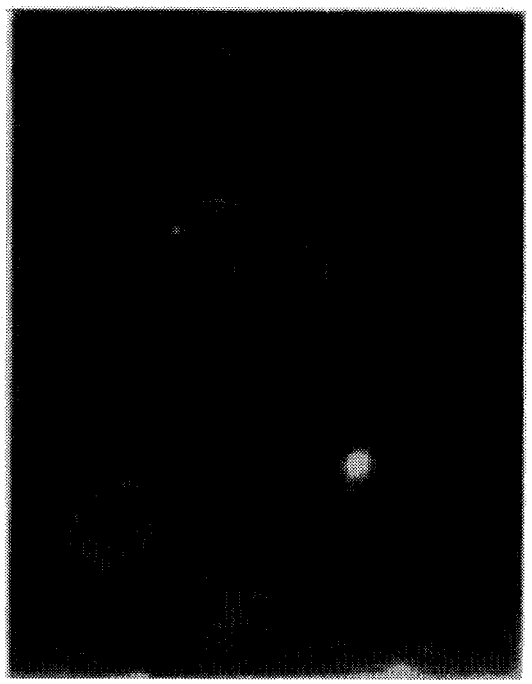
FIG. 18 (A and B) are photographs of an indirect immunofluorescent stain of p15s in cells from rabbit peritoneal exudates with (A) pre-immune and (B) immune sera.
Figure 18B:

To determine which blood cells contain p15s, fixed smears of rabbit peritoneal exudate leukocytes or rabbit peripheral blood were analyzed by indirect immunofluorescence. All PMN, both from peritoneal exudates (FIG. 18), as well as from peripheral blood (not shown), stained brightly, whereas red blood cells, lymphocytes and monocytes showed little or no fluorescence. Staining of PMN within a preparation and between preparations from different rabbits was similar in intensity, confined to the cytoplasm, and punctate.

Figure 19:
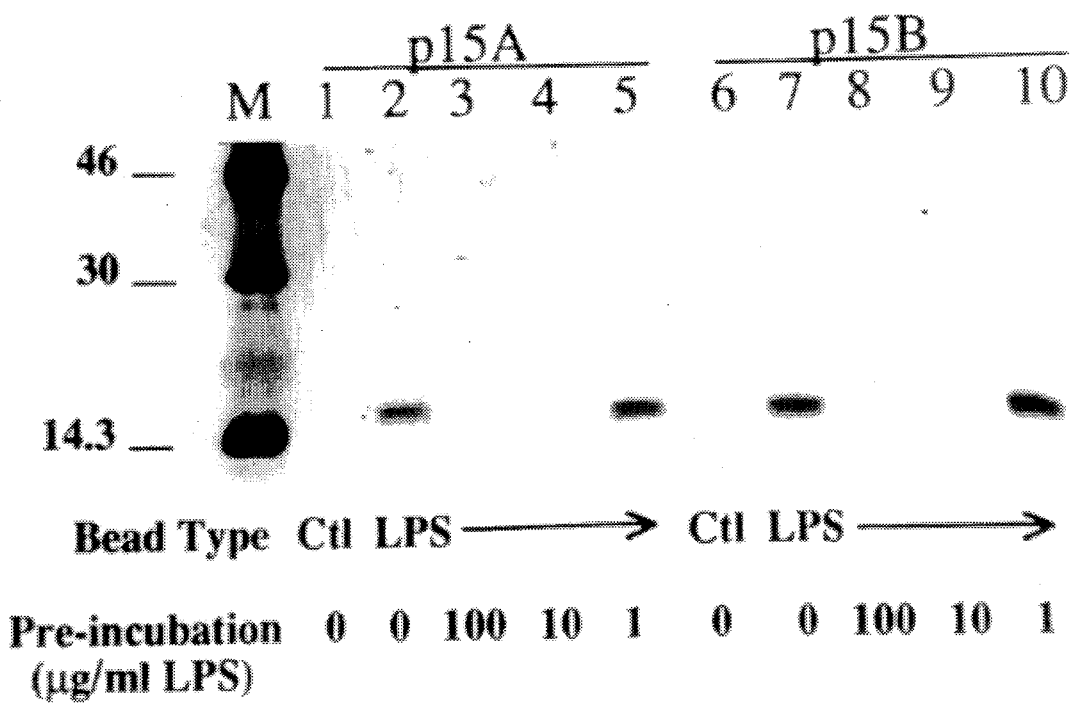
FIG. 19 is an SDS polyacrylamide gel showing the binding of p15s to LPS. Lanes 1–5: p15A; lanes 6–10: p15B.

Binding to LPS. The high affinity binding of the p15s to *E. coli* is the basis for their isolation and suggested that these strongly basic proteins are attracted to the negatively charged LPS in the outer membrane of the Gram negative envelope. To more directly assess the ability of the p15s to bind to LPS, the two isoforms purified from a single rabbit were incubated with LPS-coated magnetic beads. Both isoforms bound to LPS-coated beads but not to the control beads (FIG. 19). The proteins also bound to isolated LPS in solution since preincubation with soluble ReLPS almost completely inhibited binding of the p15s to the LPS-coated beads.

EXAMPLE 11

In order to determine whether the potentiation by the p15s of the antibacterial and anti-LPS actions of Bactericidal/Permeability-Increasing protein are also manifest in a more physiological relevant setting, the serum-resistant strain *E. coli* Klr was incubated in whole citrated human blood with either rabbit BPI (1–10,000 pM), p15A (500nM), or a combination of the two.

Figure 20:
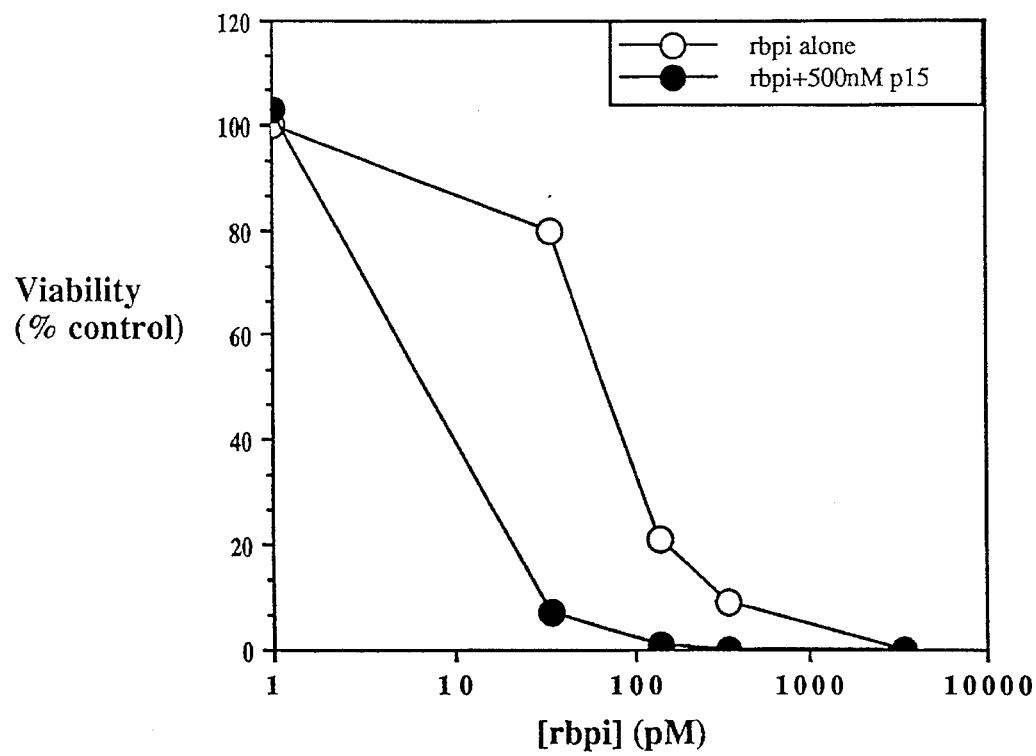
FIG. 20 is a graph showing the synergy between rabbit BPI and p15A in the growth inhibition of E. coli Klr in whole human blood ex vivo.
Figure 21:
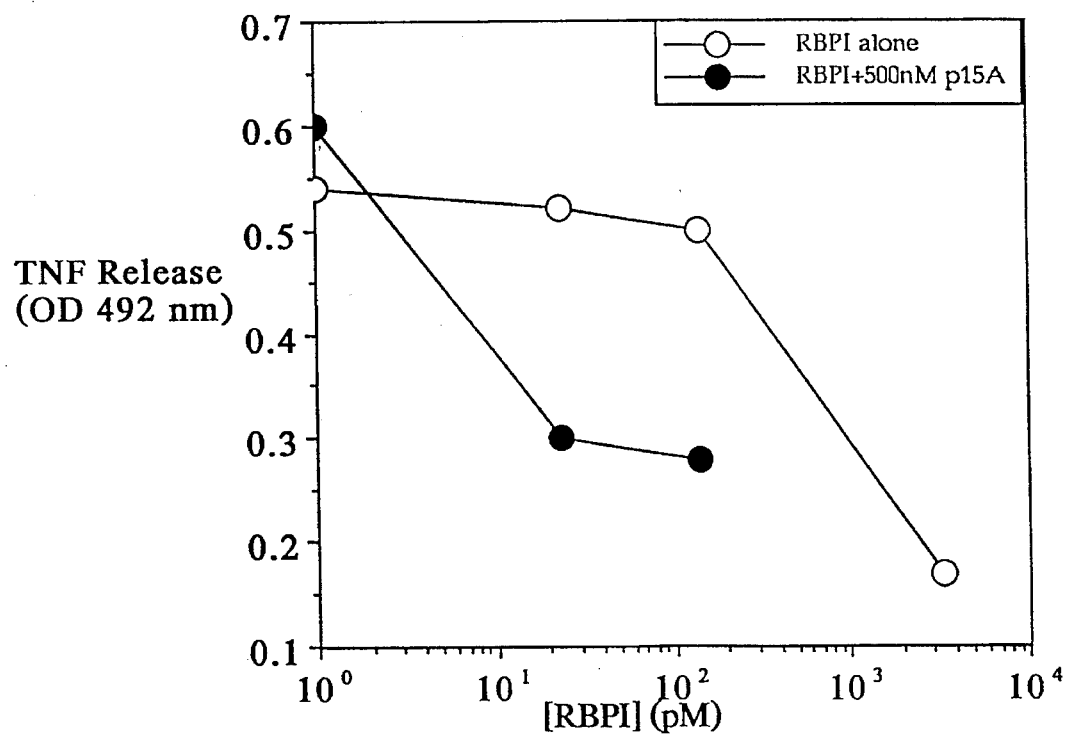
FIG. 21 is a graph showing the synergy between p15A and rabbit BPI in the suppression of TNF induction by E. coli Klr in whole human blood ex vivo.
Figure 22:
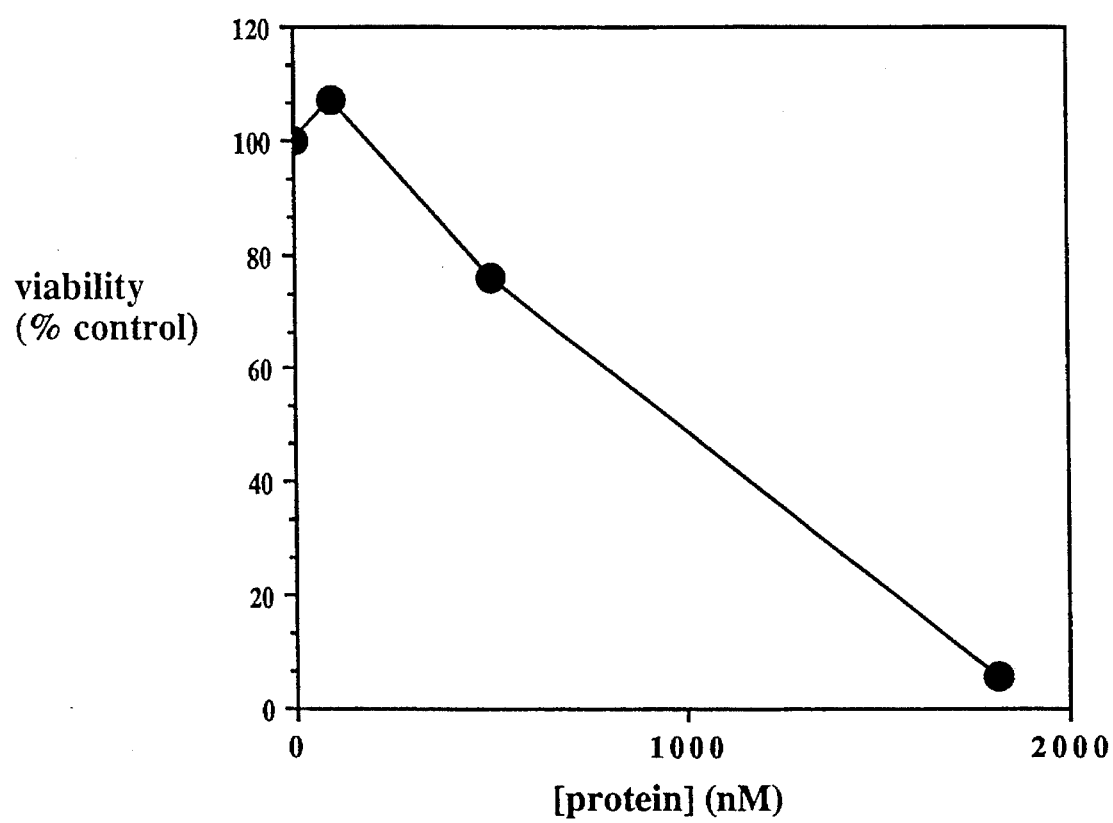
FIG. 22 is a graph showing the effect of p15 on the growth of E. coli Klr in whole human blood ex vivo.

The "A" isoform was incubated in 250 μl of citrated whole human blood (obtained from a normal subject) at 37° C. for 5h and assayed for TNF release (with $10^4$ *E. coli* Klr)

as described above or for growth inhibition (with $10^4$ E. coli Klr). The results are shown in FIGS. 20–22.

p15 "A" at 500 nM reduced by at least 10-fold the BPI dose required for growth inhibition (FIG. 20) or suppression of TNF release (FIG. 21). In addition, at higher concentrations (approximately micromolar), p15A alone also exerted independent growth inhibition of E. coli Klr (FIG. 22).

EXAMPLE 12

Two granule-associated antimicrobial proteins, identified by structural analysis as the defensins NP-1 and NP-2, are the most cationic and potent members of the family of cytotoxic peptides mentioned above. p15s, like defensins, at 10– 50 nM inhibit by >90% the growth of E. coli J5 in hypotonic media when tested in the absence of BPI, but neither manifests antibacterial activity in isotonic media when tested at concentrations up to 5000nM. However, in combination with BPI in isotonic media, both p15s ($\geq$100nM) and NPs -1 & -2 ($\geq$500nM) can reduce the concentration of BPI needed for growth inhibition of E. coli from 50nM to $\leq$2nM. The p15s and the defensins are potent inhibitors of endotoxin in isotonic media (IC50 5–50nM), as measured against Re lipopolysaccharide (LPS) in the Limulus amebocyte lysate assay and as a priming agent for release of arachidonic acid by human granulocytes. The less cationic defensins rabbit NP-5 and human HNP-2 & -4 are less potent. In marked contrast to BPI, which potently neutralizes LPS of any chemotype (IC50 0.5–2nM), neither p15s nor defensins inhibited S type LPS (0111:B4). Thus granulocytes express a number of structurally and functionally distinct cationic proteins that exhibit affinity for LPS, both isolated and within the bacterial envelope, and that can act synergistically as antibacterial agents.

What is claimed is:

1. An isolated nucleic acid comprising a DNA sequence encoding a polypeptide of mammalian origin having a molecular weight of about 15,000 daltons and bactericidal/permeability-increasing protein potentiating activity.

2. The isolated nucleic acid according to claim 1, said DNA encoding a polypeptide comprising an $NH_2$-terminal sequence of Ile—Pro—Xaa— Arg—Arg—Leu—Arg—Tyr—Glu—Glu—Val—Val—Ala—Gln—Ala—Leu—Gln—Phe—TYr—Asn, wherein Xaa is selected from the group consisting of Arg (SEQ ID NO: 1), His and Ala (SEQ ID NO:2).

\* \* \* \* \*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Ile  Pro  Arg  Arg  Arg  Leu  Arg  Tyr  Glu  Glu  Val  Val  Ala  Gln  Ala  Leu
 1                   5                        10                       15

Gln  Phe  Tyr  Asn
               20
```

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Ile  Pro  Ala  Arg  Arg  Leu  Arg  Tyr  Glu  Glu  Val  Val  Ala  Gln  Ala  Leu
 1                   5                        10                       15

Gln  Phe  Tyr  Asn
               20
```